(12) United States Patent
Hirota et al.

(10) Patent No.: US 7,955,310 B2
(45) Date of Patent: Jun. 7, 2011

(54) MEDICAL NEEDLE

(75) Inventors: Tadanobu Hirota, Nasu-Shiobara (JP);
Yoshio Higaki, Tatebayashi (JP)

(73) Assignee: Nipro Corporation, Osaka (JP)

( * ) Notice: Subject to any disclaimer, the term of this patent is extended or adjusted under 35 U.S.C. 154(b) by 1391 days.

(21) Appl. No.: 11/434,198

(22) Filed: May 16, 2006

(65) Prior Publication Data
US 2006/0271001 A1 Nov. 30, 2006

Related U.S. Application Data

(60) Provisional application No. 60/735,883, filed on Nov. 14, 2005.

(30) Foreign Application Priority Data

| May 25, 2005 | (JP) | 2005-153088 |
| Sep. 12, 2005 | (JP) | 2005-263959 |
| Mar. 20, 2006 | (JP) | 2006-077599 |

(51) Int. Cl.
*A61M 5/32* (2006.01)
*A61M 5/00* (2006.01)

(52) U.S. Cl. ........ 604/263; 604/177; 604/192; 604/197; 604/198

(58) Field of Classification Search ................. 604/177, 604/187–188, 192–193, 197–198, 206
See application file for complete search history.

(56) References Cited

U.S. PATENT DOCUMENTS

| 5,219,339 | A | * | 6/1993 | Saito | 604/198 |
| 5,591,138 | A | * | 1/1997 | Vaillancourt | 604/263 |
| D476,419 | S | * | 6/2003 | Swenson | D24/130 |
| 2005/0177112 | A1 | * | 8/2005 | Restelli et al. | 604/177 |
| 2005/0267416 | A1 | * | 12/2005 | Mohammed | 604/198 |

FOREIGN PATENT DOCUMENTS

| JP | A 63-317160 | 12/1988 |
| JP | A 2-1289 | 1/1990 |
| JP | A 4-180772 | 6/1992 |
| JP | A 11-319086 | 11/1999 |
| JP | A 2001-259029 | 9/2001 |
| JP | A 2005-518881 | 6/2005 |
| WO | WO 93/01851 | 2/1993 |

* cited by examiner

*Primary Examiner* — Nicholas D Lucchesi
*Assistant Examiner* — Quynh-Nhu H Vu
(74) *Attorney, Agent, or Firm* — Oliff & Berridge, PLC

(57) ABSTRACT

To provide a syringe in which a covering member whose engagement has been released automatically moves to a projection movement terminal where it can be prevented from returning, and returning of a projection positioned at the projection movement terminal can be limited.

A covering member 6 is formed so as to be guided by a guide portion 4e to a stopper portion 4h from its housed posture within a holding portion main body 4c so that a projection 6a engages with an engagement portion 4f while being urged by a spring 7 to a covering posture so that the engagement is released and the covering member covers a needle exposed portion 2a, a return preventive portion 4j is joined from a stopper portion 4h toward the base end, and furthermore, a returning movement limiting portion 4m is formed at a holding portion main body 4c so as to be positioned closer to the base end side than the stopper portion 4h and closer to the tip end side than the returning movement terminal 4w of the return preventive portion 4j while being spaced to the base end side from the projection 6a positioned at the stopper portion 4h so as to face the projection while leaving a space S, and comes into contact with the projection 6a lifted from the stopper portion 4h within the range of the space S.

8 Claims, 30 Drawing Sheets

(A)

(B)

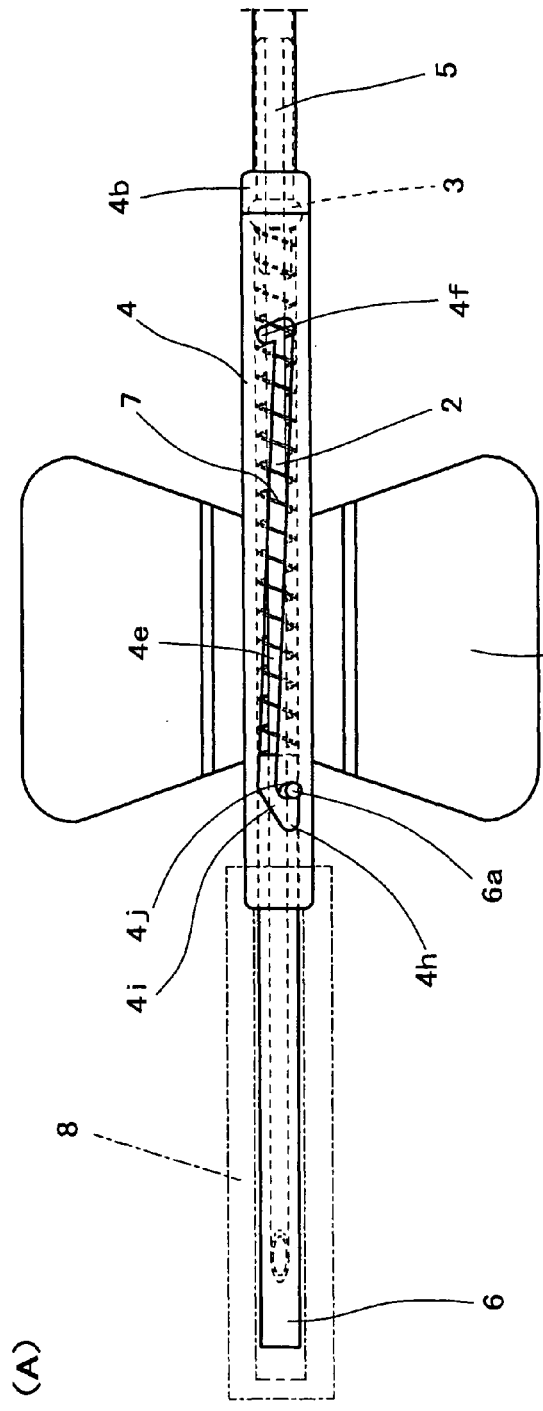
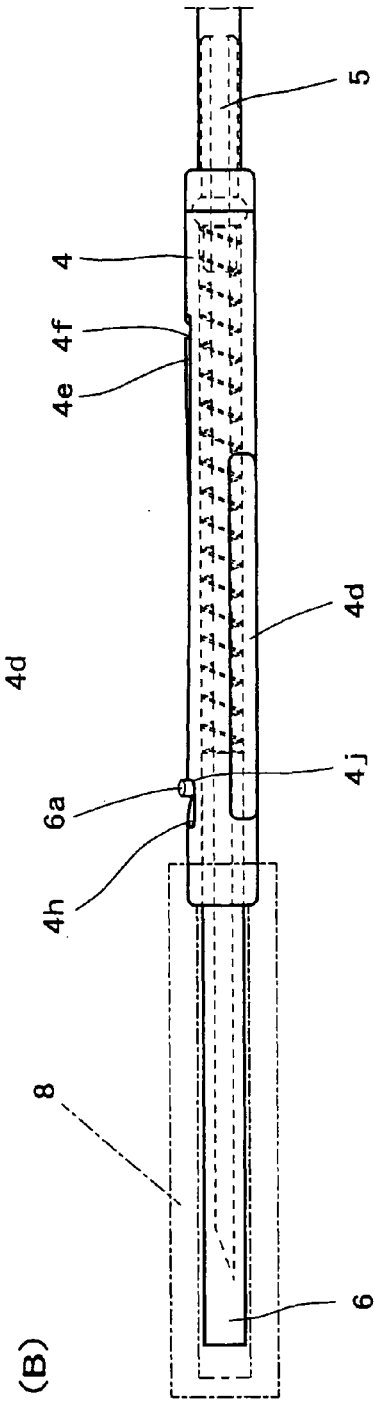
Fig.2 (A)
Fig.2 (B)

(A)

(B)

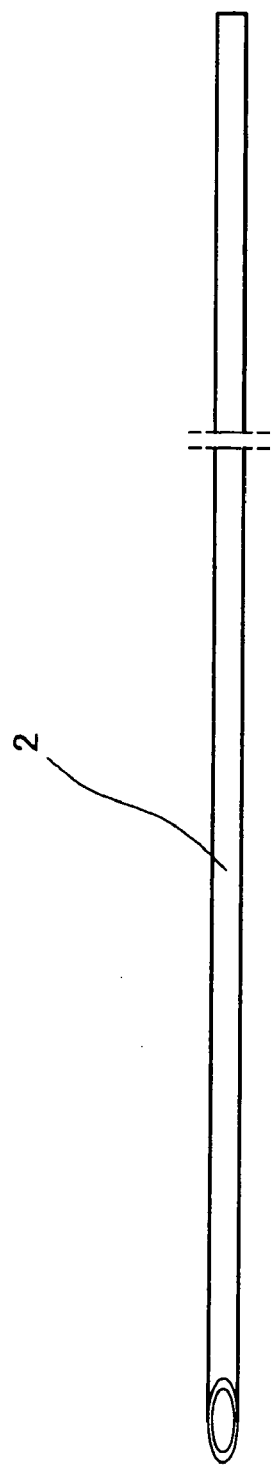
Fig.5 (A)
Fig.5 (B)

(A)

(B)

(C)

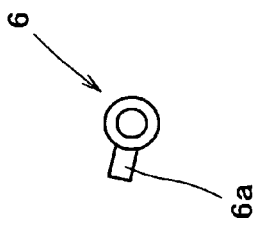
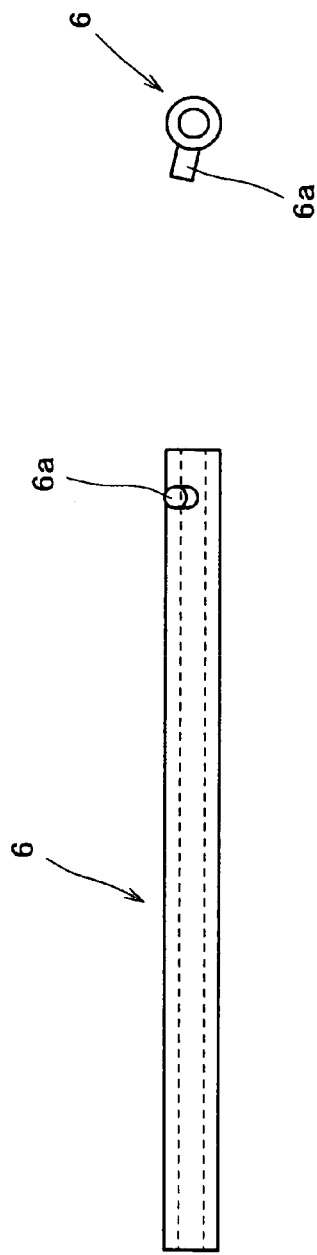
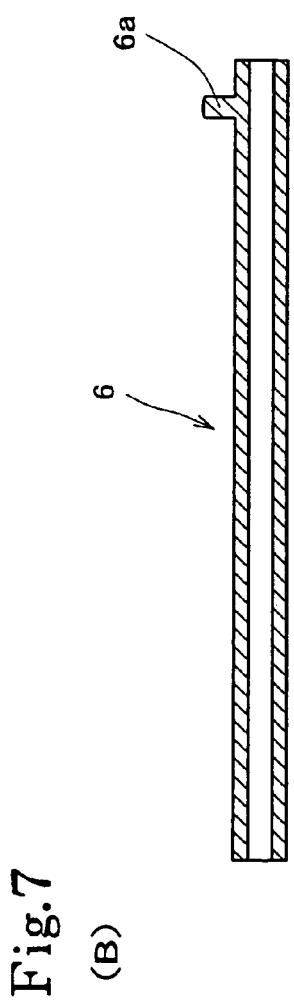

(A)

(B)

(A)

(B)

(A)

(B)

(A)

(B)

(A)

(B)

(C)

(A)

(B)

(A)

(B)

(A)

(B)

(A)

(B)

(A)

(B)

(C)

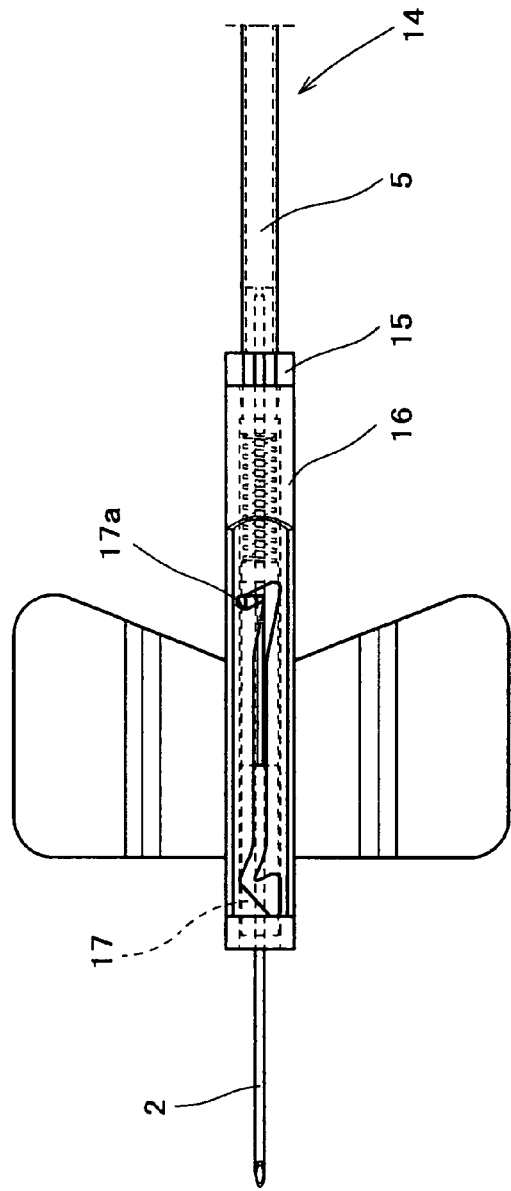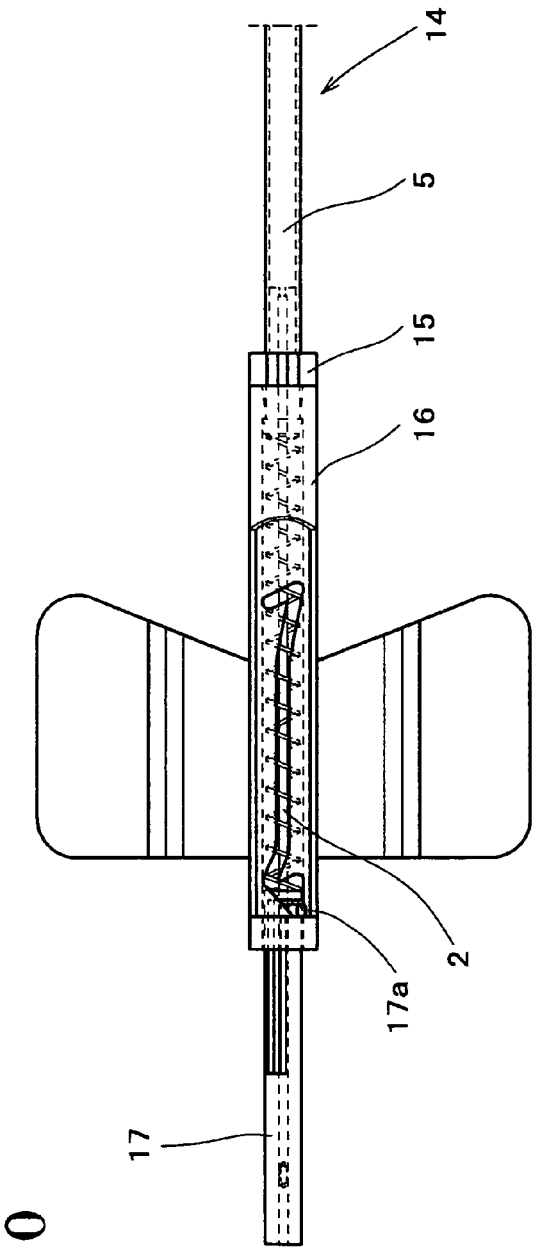
Fig.20 (A)
Fig.20 (B)

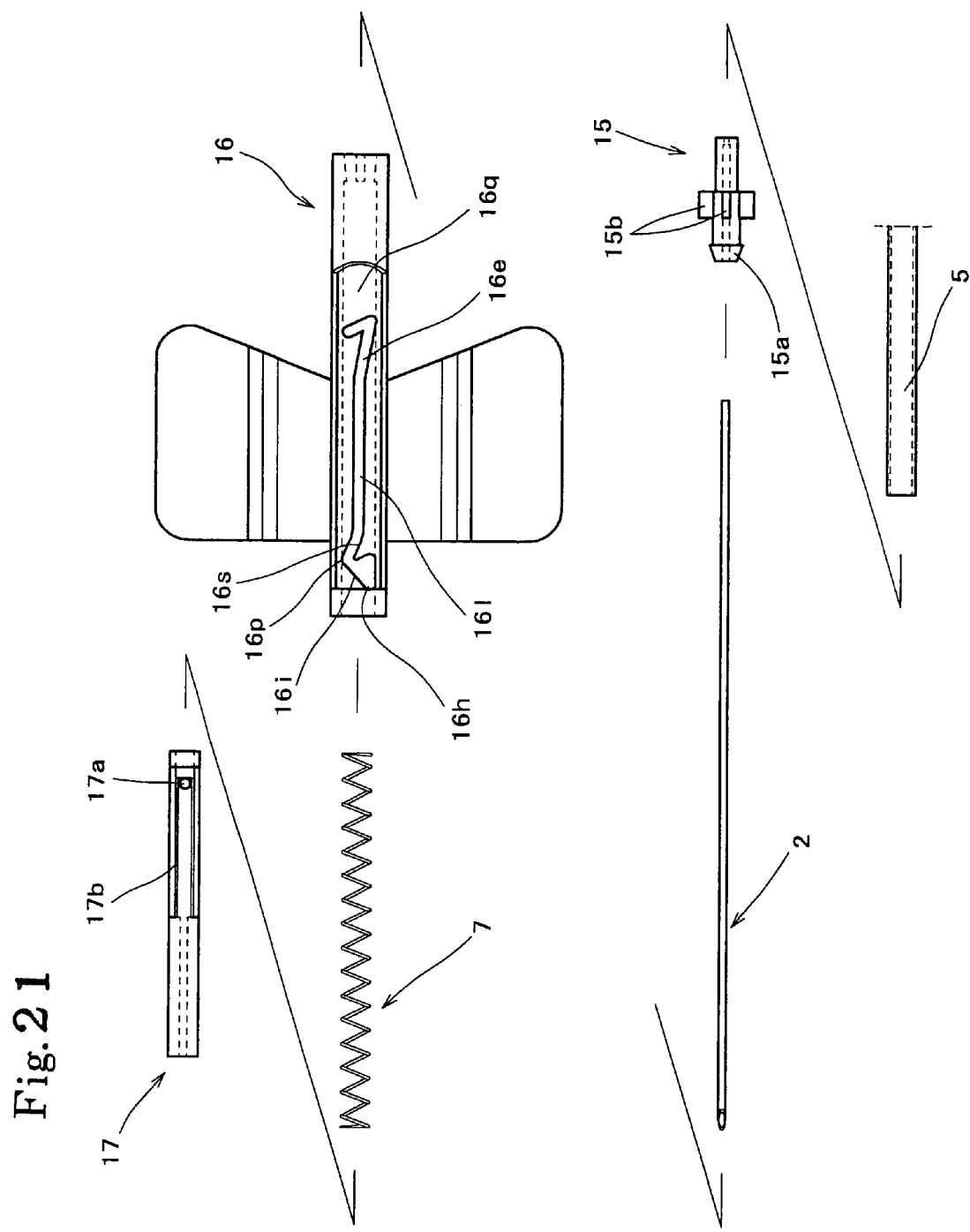

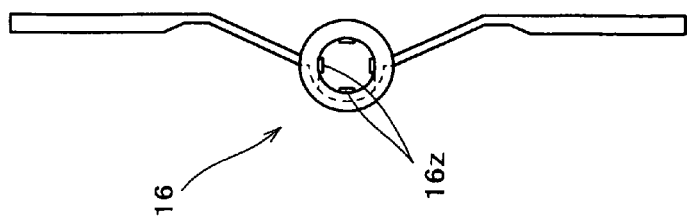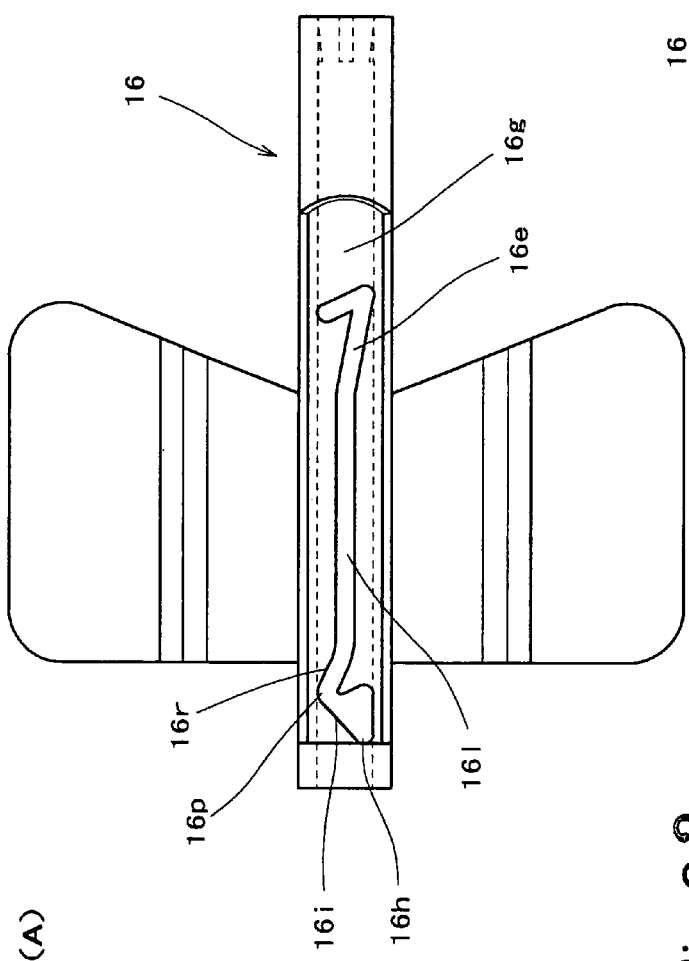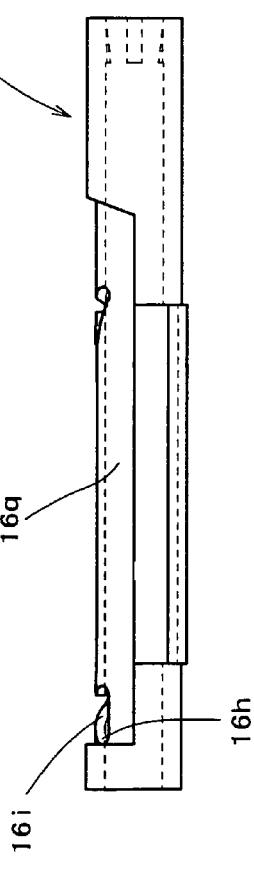

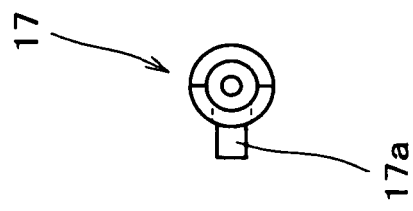
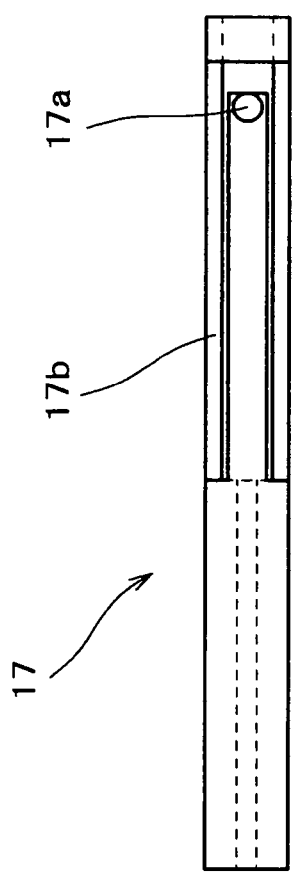
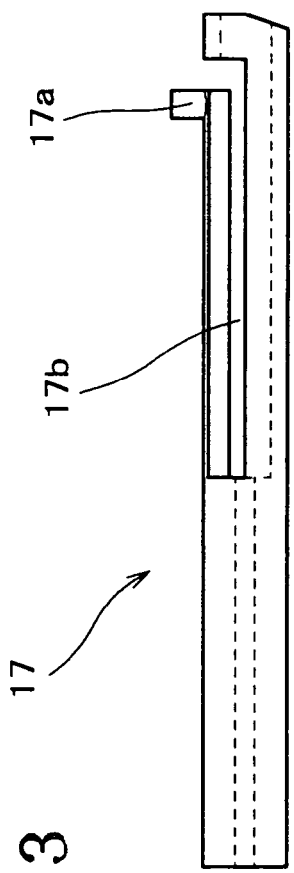

(A)

(B)

(C)

Fig.26 (A)
Fig.26 (B)
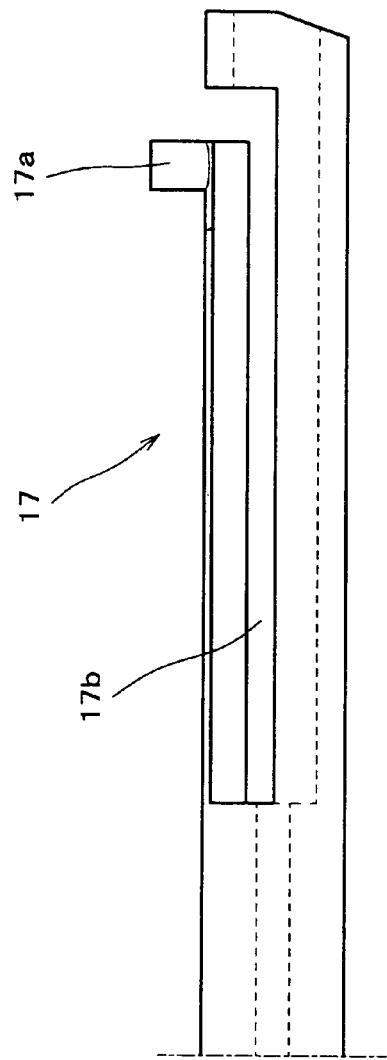
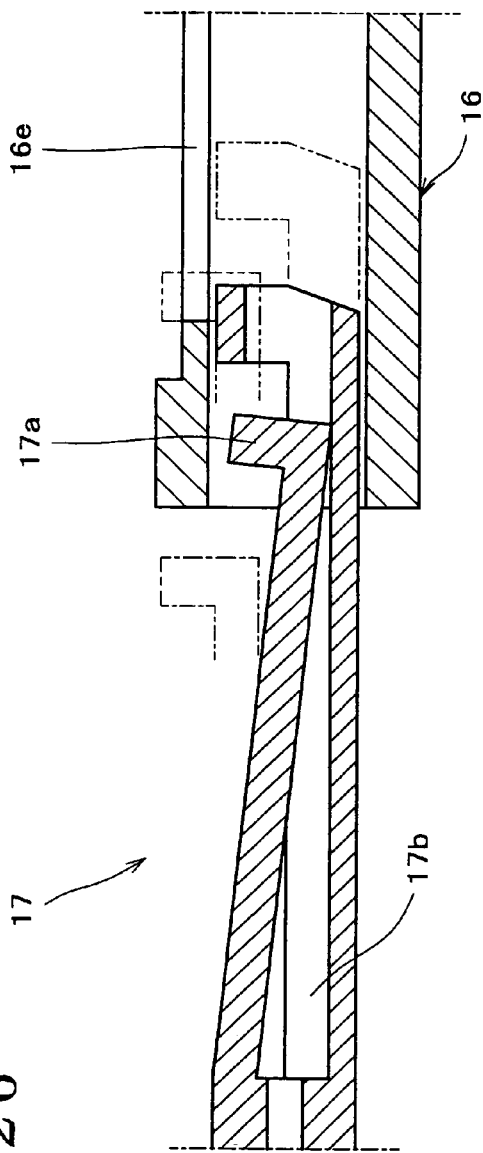

MEDICAL NEEDLE

The present invention belongs to the technical field of a medical needle unit which is used for medical purposes such as injections, drips, and blood transfusions, etc., and whose needle can be covered and safely disposed of after being used.

BACKGROUND ART

Generally, such medical needle units include a needle unit like a butterfly needle structured by supporting the base end of the needle by a support member provided with a pair of wings, and such a needle unit is used by fixing the wings to a human body by an adhesive tape while inserting a needle into the human body. After such a needle is used, if the needle tip is left exposed, it may stick into other persons by mistake.

Therefore, there are needle units in which a cylindrical covering member is freely fitted to a tube that communicates and joins the needle and a medical container to each other, and after use, the needle unit is safely disposed of by covering the needle by the covering member (for example, refer to Patent Document 1).

Furthermore, there are needle units in which a holding member is movably and externally fitted with a covering member or a covering member is movably fitted to the inner side of the holding member so as to cover the needle after being used (for example, refer to Patent Documents 2 and 3).

However, these require a doctor or a nurse to move the covering member to the tip end of the needle to cover the needle, so that the operations are troublesome, and in addition, in a state that the needle is exposed, the covering member is movable toward the needle, so that after the needle is stuck into a human body, the covering member will move toward the tip end of the needle until the wings are fixed by tape. Furthermore, when moving the covering member to cover the needle, if the tape is not completely peeled off and still stuck between the covering member and the holding member, the covering member cannot move, which will be a problem.

Therefore, a needle unit is proposed in which the holding member is provided while leaving a space between the needle so that the covering member provided movably in the space between the holding member and the needle can automatically move from its housed posture to a covering posture by receiving an urging force of a spring, and the covering member moved to the covering posture is prevented from returning when it is pushed back (for example, refer to Patent Document 4).

However, because this returning prevention is realized by providing a return preventive guide so as to project in an elastically returnable manner near the terminal of the moving path of a projection provided on the covering member, the return preventive guide narrows the moving path of the projection, and the projection is required to forcibly move beyond the return preventive guide against the restoring force near the terminal of the movement of the covering member from the housed posture to the covering posture.

When the needle is thus covered by the covering member after the needle is used, in addition to the use in which the needle is pulled out from a patient and the engagement of the covering member in its housed posture is released to cover the needle, use in a slowly moving state so that the covering member in the housed posture is disengaged before pulling-out the needle from a patient and the needle is gradually pulled out while the tip end of the covering member is pressed against the skin of the patient, the needle is covered by the covering member in time with the pulling-out of the needle, and to reliably make the projection to forcibly move beyond the return preventive guide and turn into the covering posture even in such use, the urging force of the spring for moving the covering member to the covering posture sufficient to only move to the covering posture at the movement terminal from the housed posture is not sufficient, and an urging force for forcibly moving the covering member beyond the return preventive guide in the slowly moving state is necessary. Accordingly, the urging force of the spring becomes strong, and as a result, the covering member collides against the movement terminal and stops, and this causes not only a shock but also a loud collision noise and discomfort for the patient, the doctor, and the nurse.

[Patent Document 1] Japanese Published Unexamined Patent Application No. H11-319086
[Patent Document 2] Japanese Published Unexamined Patent Application No. H04-180772
[Patent Document 3] Japanese Published Unexamined Patent Application No. 2001-259029
[Patent Document 4] WO2003/074117
[Patent Document 5] Japanese Published Unexamined Patent Application No. H02-1289
[Patent Document 6] Japanese Published Unexamined Patent Application No. S63-317160

DISCLOSURE OF THE INVENTION

Problem to be Solved by the Invention

Particularly, patients' blood and body fluids adhere to the needle after use of the medical needle unit, and secondary infection of medical staff such as doctors and nurses or waste disposers who dispose of medical waste caused by touching such a needle by mistake has become a large social issue. Particularly, careful handling to prevent touching of needles is needed for needle units used for patients who suffer from serious diseases such as HIV or hepatitis, so that the needle unit which requires a strong spring urging force to realize the forcible movement has a possibility that blood or the like adhering to the needles splatter around due to an impact when the projection reaches the movement terminal, and this is the problem that the prevent invention solves.

On the other hand, in the field of needle units, needle units structured so that needles are covered after use have been proposed (for example, Patent Documents 5 and 6). However, these are not structured so as to automatically move the covering member into a covering posture by receiving a spring urging force, but are structured to manually move it, and this accordingly places a great burden on the medical staff, and some are structured so as to have a return preventive guide as in the case of the Patent Document 5, however, in this type, the covering member reaching its movement terminal must be manually rotated circumferentially and moved to a return preventive position, and if failing to do this operation, the return preventive function will not be performed and the needle is easily returned into an exposed state. This is also a problem that the prevent invention solves.

Means for Solving the Problem

In view of the above-described circumstances, the present invention was developed for solving these problems, and according to the invention, a medical needle unit comprises: a hollow needle; a holding member formed so that its base end holds the needle base end and its main body covers the needle while leaving a space between the same and the needle, and the needle tip end sticks out from the main body tip end; a covering member that is provided in the space between the holding member main body and the needle, and is movable with respect to the holding member between a housed posture on the base end side in which the covering member is housed within the holding member main body while the needle tip end sticks out from the holding member main body and a covering posture on the tip end side in which the covering member sticks out from the holding member main body and covers the needle tip end; a guide portion that is formed on the holding member main body so as to guide a projection formed on an outer peripheral surface of the covering member and enable the covering member to move between the housed posture and the covering posture; an engaging mechanism that disengageably engages with the projection and holds the covering member in the housed posture, and allows the movement from the housed posture to the covering posture of the covering member according to disengagement of the projection; and an urging member that forcible moves the covering member the projection of which has been disengaged to the covering posture until the projection reaches the projection movement terminal of the guide portion, wherein when a force to push-back the covering member positioned at the projection movement terminal to the base end side is applied according to forcible movement by the urging member, in order to prevent the covering member from moving to the base end side and prevent the needle tip from being exposed from the covering member, the guide portion comprises a first guide portion joined to the engaging mechanism at the base end and formed to be a slot-shaped and long in the lengthwise direction of the needle and a second guide joined from the first guide tip end in an inclined shape or curved shape circumferentially and guides the projection through the first guide to the projection movement terminal while leading this circumferentially with respect to the holding member, and the holding member main body is provided with a return preventive guide that faces the projection movement terminal while being positioned closer to the second guide side than the first guide tip end, and allows the projection to return to the base end side within a range that the needle tip does not stick out from the covering member when a force is applied to push-back the covering member whose projection is positioned at the projection movement terminal to the base end side, and a returning movement limiting portion that is positioned closer to the base end side than the projection movement terminal and closer to the tip end side than the returning movement terminal of the return preventive guide, positioned at the tip end side of the first guide while being spaced toward the base end side from the projection positioned at the projection movement terminal, and restricts the returning movement of the projection toward the first guide side, the returning movement limiting portion restricting the returning movement of the projection toward the first guide side by contacting with the projection when a force to push-back the covering member toward the base end side is applied and the projection positioned at the projection movement terminal moves toward the first guide tip end side.

According to the invention of claim 2, in claim 1, a movement urging portion that urges the projection to move to the returning movement terminal is provided between the returning movement limiting portion and a returning movement terminal of the return preventive guide.

According to the invention, in the medical needle unit of claim 1 or 2, the returning movement limiting portion is a tip end portion of the first guide.

According to the invention, the second guide is provided with a return restricting portion on the opposite side to the leading side to the second guide in the circumferential direction with respect to the first guide, said return restricting portion restricting the projection from moving to the opposite side of the circumferential direction over the first guide tip end position and returning to the first guide when the projection is doing returning-back movement while sliding and contacting on the second guide.

Effects of the Invention

According to the invention, when the covering member moves from the housed posture to the covering posture, the projection is led circumferentially at a stage before the guide portion movement terminal, and when the projection reaches the guide portion movement terminal, due to said leading, the projection faces the return preventive guide formed by being folded back from the guide portion movement terminal. As a result, when a force to push-back the covering member in the covering posture is applied, the projection does not return to the guide portion side but moves to the return preventive guide and the needle tip is prevented from being exposed from the covering member, so that the projection is not needed to forcibly move over the elastically restorable return preventive member, and therefore, when the projection reaches the guide portion movement terminal, the spring can be turned into a natural state or made close to this state, whereby the covering member can be moved to the covering posture with less shock and smaller uncomfortable noise. Furthermore, a returning movement limiting portion is formed closer to the first guide side than the movement terminal while being spaced from the projection positioned at the projection movement terminal, and even if the projection positioned at the projection movement terminal returns while rotating circumferentially, the returning movement of the projection is limited by contact of the projection with the returning movement limiting portion, and therefore, the covering member in the covering posture can be effectively prevented from returning to the housed posture side to a degree at which the needle is exposed. As a result, when the medical needle unit after use is disposed of, infection or the like caused by touching the exposed needle can be prevented.

According to the invention, when the projection moved from the projection movement terminal to the base end side comes into contact with the returning movement limiting portion, the projection is urged to move toward the returning movement terminal side, and the returning movement of the covering member to the base end side can be more effectively prevented, and the needle after use can be more effectively prevented from being exposed.

According to the invention, the returning movement limiting portion can be provided long circumferentially.

According to the invention, when the projection moves from the projection movement terminal to the base end side while being in contact with the second guide, the projection enters the return restricting portion and is prevented from returning to the first guide side, whereby the needle after use can be more effectively prevented from being exposed.

BEST MODE FOR CARRYING OUT THE INVENTION

Next, a first embodiment of the invention will be described based on FIGS. 1 through 15. In the drawings, the reference numeral 1 denotes a medical needle unit, and this needle unit 1 is structured so that a hollow needle 2 having a sharp tip end is held by a holding member 4 via a support member 3 fixed and fitted around the base end 23 of the needle 2. In this embodiment, the support member 3 includes a main body 3a formed into a cylindrical shape in which the base end 23 of the needle 2 is inserted and fixed and a convex portion 3b swelling out to the outer peripheral surface of the main body 3a.

On the other hand, the holding member 4 includes a holding portion 4a that holds in a clipping manner the convex portion 3b between the same and a lid 4b, and a holding portion main body 4c extending to the needle tip end side from the holding portion 4a, and a pair of wings 4d that freely open and close are projectedly formed on the outer peripheral surface of the holding portion main body 4c. The needle 2 has, on its tip end side, an exposed portion 2a sticking out from the holding portion main body 4c so as to be stuck into a human body, and around a portion sticking out from the lid 4b of the support member 3, a tube 5 to be connected to a medical solution container is fitted and fixed.

The holding portion main body 4c is constructed so as to leave a space between its inner peripheral surface and the outer peripheral surface of the needle 2, and in this space, a cylindrical covering member 6 is interposed freely movably in the lengthwise direction of the needle. The covering member 6 is formed so that a projection 6a is projectingly formed on the base end outer peripheral surface, and in the holding portion main body 4c, a guide portion 4e for guiding the projection 6a that has been disengaged as described later to a covering posture so that the covering member 6 covers the needle exposed portion 2a is formed in a slot shape long in the lengthwise direction of the needle 2.

To the base end of the guide portion 4e, an engagement portion 4f is joined by folding so as to continue in the circumferential direction of the holding member 4 from the guide portion 4e, and the engagement portion 4f is used as an engaging mechanism in which the projection 6a engages and disengages in a state of sticking out from the outer peripheral surface of the holding portion main body 4c. The covering member 6 is positioned (set) in a housed posture so as not to project from the tip end of the holding portion main body 4c, that is, positioned within the holding portion main body 4c. In addition, the covering member 6 is always urged toward the tip end side, that is, the covering posture side (tip end side) by a coil type spring 7 interposed in a compressed manner between the base end of the covering member 6 and the holding portion 4a. By moving the projection 6a projecting from the holding portion main body 4c toward the guide portion 4e side by a nail or finger, the engagement of the projection 6a with the engagement portion 4f is released, whereby the covering member 6 moves toward the tip end side by receiving an urging force of the spring 7 while the projection 6a is guided by the guide portion 4e.

As the engagement portion 4f, as shown in FIG. 12, various shapes such as one folded toward the tip end side in an inclined shape having an angle, one folded back at right angles from the base end of the guide portion 4e, and one bent in a U shape toward the tip end side, are possible. In these cases, a resistant portion 4g that narrows the hole width in order to restrict unexpected movement of the projection 6a from the engagement portion 4f to the guide portion 4e side can be formed.

In this embodiment, a certain portion of the projection 6a of the covering member 6 must be forcibly incorporated and fitted in the guide portion 4e, and for this, it is possible that the covering member 6 is made of a flexible material and forcibly fitted in an elastically deforming manner, however, as shown in FIGS. 13 and 14, by providing a slit 6b in the covering member 6, the projection 6a can be made easier to elastically deform the certain portion.

The covering member 6 whose projection 6a has been disengaged from the engagement portion 4f moves in a state that the projection 6a is guided by the guide portion 4e and the projection 6a comes into contact with the projection movement terminal 4h formed on the tip end of the guide portion 4e and is positioned in a covering posture while the projection 6a contacting with the projection movement terminal 4h restricts further movement of the covering member 6, and holds the covering member 6 so as to prevent it from coming off the holding portion main body 4c. The covering member 6 in this state is positioned in a covering posture for covering the needle exposed portion 2a. The stopper portion 4h is formed to have a second guide 4i inclined toward the tip end side in the circumferential direction of the guide portion 4e. Incidentally, the guide section of the guide portion 4e on the tip end side joined to the base end side of the second guide 4i is formed long in the lengthwise direction of the needle and becomes a first guide 4l that guides the projection 6a from the engagement portion 4f to the second guide 4i. Then, the guide portion 4e is formed wider in the whole length than the projection 6a and guides the projection 6a to the second guide 4i with almost no reduction in speed, however, the second guide 4i reduces the speed of the projection 6a while slidingly contacting on the tip end side surface (side surface on the upper side of FIG. 1) and leads it to the projection movement terminal 4h. The second guide 4i of this embodiment is formed straight, and can reduce the speed of the projection 6a reaching the second guide 4i by coming into contact with it. Incidentally, as a matter of course, the second guide 4i can also be formed in a curved shape. On the stopper portion 4h, a slot-shaped return preventive guide 4j is formed by being folded back toward the base end side so as to prevent the projection 6a from returning to the second guide 4i when the covering member 6 positioned in the covering posture is moved to the base end side (housed posture side), and the covering member 6 is restricted from further moving toward the base end side due to contact of the projection 6a with the base end of the return preventive guide 4j, that is, a returning movement terminal 4w when the covering member 6 receives a load in the returning direction, whereby the tip end of the needle exposed portion 2a is prevented from returning while it is not exposed from the covering member 6. The guide portion 4e side (the second guide 4i side) of the returning movement terminal 4w of the return preventive guide 4j projects toward the tip end while avoiding the guide portion 4e so as not to become resistant when guiding the projection 6a by the guide portion 4e, which urges the projection 6a so as to securely prevent it from returning by the return preventive guide 4j, and prevents the projection 6a engaging with the returning movement terminal 4w from sliding toward the guide portion 4e side and returning to the housed posture.

Furthermore, sometimes there happens such a case that the covering member 6 in the covering posture is pushed back toward the base end side 22 while receiving a load of rotating toward the first guide 4l side and then the projection 6a positioned at the projection movement terminal 4h moves in the returning direction while being displaced to the continuing section 4p between the tip end of the first guide 4l and the base end of the second guide 4i from the projection movement terminal 4h. And in this case, a movement limiting portion 4m is formed which is positioned closer to the base end side 22 than the projection movement terminal 4h, positioned closer to the tip end side 21 than the returning movement terminal 4w of the return preventive guide 4j, and positioned on the first guide 4l side while facing the projection 6a positioned at the projection movement terminal 4h and spaced from the projection 6a toward the base end side 22, that is, having a space S on the base end side 22 from the projection 6a, that is, positioned (displaced) on the continuing portion 4p side. Then, when the covering member 6 is pushed back to the base end side 22 while receiving a load of rotating toward the first guide 4*l* side, contacted by the projection 6*a* lifted from the projection movement terminal 4*h* and limits the returning movement of the projection 6*a* to the first guide 4*l* through the continuing section 4*p*.

Namely, the returning movement limiting portion 4*m* of this first embodiment is positioned (displaced) adjacent to the continuing section 4*p* side of the return preventive guide 4*j* and projectingly formed and sharpened toward the tip end side so as to form the returning movement terminal 4*w* in an inverted U groove shape. When the projection 6*a* is lifted while receiving a load of rotation to the continuing section 4*p* side and the projection 6*a* comes into contact with the tip end 4*n* of the returning movement limiting portion 4*m* in a rotating state within a range without exceeding the circumferential half from the projection movement terminal 4*h*, the returning movement limiting portion limits the movement of the projection 6*a* to the continuing section 4*p* side and leads it to the returning movement terminal 4*w* side, and in the rotative movement within this range, the projection 6*a* is prevented from moving to the first guide 4*l* side through the continuing section 4*p* and the needle from being exposed.

The returning limiting portion 4*m* of this embodiment is formed so as to have an arc tip end as shown in FIG. 11(A), however, it is not limited to this, and for example, it can also be formed into a pointed shape like the embodiment shown in FIG. 11(B).

Furthermore, the projection 6*a* of this embodiment is formed in a columnar shape. That is, as long as it can be guided by the guide portion 4*e*, it can be formed in rectangular column, or triangular column, as shown in FIG. 15(A). It can also be formed in a half column, by forming the chord portion inclined opposite the second guide 4*i* into a half column facing the movement limiting portion 4*m* side like the embodiments shown in and FIG. 15(B). In this case, the chord portion of the projection 6*a* in contact with the limiting portion tip end 4*n* is led to the returning movement terminal 4*w* side and the returning limit range is broadened, and the return preventive function can be improved.

The guide portion 4*e* of this embodiment is communicated with the engagement portion 4*f* on the upper side in view of FIG. 1 and reaches the second guide 4*i* while inclined to the tip end side of the engagement portion 4*f* side (upward) from the communicating position, and the second guide 4*i* is formed by being folded downward to the tip end side so as to provide a space in which the return preventive guide 4*j* can be formed on the base end side of the projection movement terminal 4*h*, so that the vertical width of the entirety of the guide portion 4*e* becomes almost equal to the vertical width of the engagement portion 4*f* necessary for engagement and disengagement of the projection, and the hole width of the guide portion 4*e* is broader than the projection 6*a*, so that the vertical width of the entire slot consisting of the engagement portion 4*f*, the guide portion 4*e*, and the return preventive guide 4*j* can be made as narrow as possible, and die forming of the cylindrical holding member 4 having this entire slot becomes easier.

The reference numeral 8 denotes a cap for covering the needle exposed portion 2*a* of the unused needle unit 1, and this cap 8 is in a cylindrical shape whose base end is opened and tip end is closed, and is attached by fitting the opening to the section closer to the tip end side than the wings 4*d* of the holding portion main body 4*c*. The needle unit 1 is used by removing the cap 8, and after use, the cap 8 can be attached again to the tip end of the holding portion main body 4*c* so as to externally fit to the covering member 6 covering the needle exposed portion 2*a*.

In the first embodiment of the invention constructed as described above, in the medical needle unit 1, the covering member 6 disposed in the space between the needle 2 and the holding portion main body 4*c* is guided and forcibly moved by the guide portion 4*e* from the housed posture within the holding portion main body 4*c* due to engagement of the projection 6*a* with the engagement portion 4*f* while being urged by the spring 7 to the covering posture so that the engagement is released and the covering member covers the needle exposed portion 2*a*. Because the guide portion 4*e* is entirely formed wider than the projection 6*a*, the second guide 4*i* of the guide portion 4*e* is formed by inclining in the circumferential direction of the holding portion main body 4*c* so as to lead the projection 6*a* to the projection movement terminal 4*h*, and the return preventive guide 4*j* is formed toward the base end from the projection movement terminal 4*h* in a communicating manner when the covering member 6 is moved from the housed posture to the covering posture, the projection 6*a* receives almost no resistance until it reaches the second guide 4*i* of a stage before the projection movement terminal 4*h*, and when it reaches the second guide 4*i*, it is led to the projection movement terminal 4*h* while slidingly contacting on the side surface of the second guide 4*i* and receiving a resistance. The projection 6*a* reaching the projection movement terminal 4*h* faces the return preventive guide 4*j* folded back from the projection movement terminal 4*h*. In this state, when a force of pushing-back is applied to the covering member 6 in the covering posture, the projection 6*a* does not return to the guide portion side but moves to the return preventive guide 4*j* and the needle tip is prevented from being exposed from the covering member 6. As a result, the spring 7 can be turned into a natural state or close to the natural state when the projection 6*a* reaches the projection movement terminal 4*h*, so that the covering member 6 can be moved to the covering posture in a state with less shock and smaller uncomfortable noise.

Furthermore, the returning movement limiting portion 4*m* is formed at the holding portion main body 4*c* in such state that it is positioned closer to the base end side 22 than the projection movement terminal 4*h* and closer to the tip end side 21 than the returning movement terminal 4*w* of the return preventive guide 4*j*, and spaced to the base end side so as to face the projection 6*a* positioned at the projection movement terminal 4*h* while leaving the space S. With this arrangement, the returning movement limiting portion 4*m* receives the contact of the projection 6*a* which has been lifted from the projection movement terminal 4*h* within the range of the space S and limits the returning movement of the projection 6*a* to the first guide 4*l* through the continuing section 4*p*. Therefore the returning movement of the covering member 6 can be restricted when the covering member 6 is pushed back to the base end side 22 while receiving a load of rotation to the first guide 4*l* side, whereby the exposure of the needle 2 can be prevented.

Incidentally, it is also considered that the projection 6*a* is caught by a finger and returned to the engaging position, however, this can be prevented by forming a section near the engagement portion of the holding portion main body 4*c* into a thick portion 4*k* projecting to a degree equivalent to or higher than the projection 6*a* so as to disable the movement of the projection 6*a* caught by the finger to the engagement portion 4*f*.

As a matter of course, the invention is not limited to the embodiment described above, and it can be carried out in the following embodiments. First, in a second embodiment shown in FIGS. 17 and 18, the needle 2 is held directly by the holding member 9 without using the support member 3.

Namely, in these types, the holding portion 9a formed on the base side of the holding member 9 is sealed (closed), and here, a through hole 9b for penetrating the needle 2 is formed so that the penetrating needle 2 can be directly fixed (for example, fixed by an adhesive agent), and a tube 10 is externally fitted and fixed to the penetrating needle 2. Thereby, the support member 3 and the lid 4b needed in the first embodiment become unnecessary, and the number of parts can be reduced.

In addition, the needle unit of a third embodiment shown in FIG. 19 is an example using the parts of the first and second embodiments. Namely, in this needle unit, an engaging projection 12 is formed which fits and engages in an engaging hole 11b formed in the covering member 11 in a lightly press-fitting manner, and an engaging hole 13a which the engaging projection 12 is fitted and engaged in is formed in the holding member 13, and the base end of the needle 2 is directly penetrated and fixed through the holding portion 13b formed at the base end of the holding member 13 without necessity of the support member 3 of the first embodiment, whereby reducing the number of parts.

In this needle unit, a stopper projection 11a projectingly provided on the covering member 11 is guided by a guide portion 13c formed on the holding member 13, and after use, when the engaging projection 12 is extracted from the covering member 11, the covering member 11 automatically moves to the covering posture from the housed posture while the stopper projection 11a is guided by the guide portion 13c, and engages with a stopper portion (not shown) at the tip end of the guide portion 13c and stopped and restricted from further movement.

In this needle unit, the stopper projection 11a can be set at a lower height so as not to project from the outer peripheral surface of the holding member 13, and thereby, the stopper projection 11a can be prevented from being caught by a finger and forcibly moved to the base end side.

The medical needle unit 14 of a fourth embodiment shown in FIG. 20 through FIG. 29 is an example using the parts of the first embodiment. Namely, in this needle unit, a thin portion 16q is formed on the outer peripheral surface of the holding portion 16, and a guide portion 16e is formed on the thin portion 16q. The guide portion 16e includes a first guide 16l and a second guide 16i inclined rightward in FIG. 29. A speed reducing portion 16r for leading a projection 17a formed on the covering member 17 in the circumferential direction in sliding and contacting manner to reduce its speed is formed at the tip end of the first guide 16l opposite the inclination direction of the second guide 16i, and a continuing section 16p is formed in a folded shape between the speed reducing portion 16r and the second guide 16i so as to communicate these. The projection movement terminal of the second guide 16i, that is, the projection movement terminal 16h which the projection 17a automatically moves to and is stopped at, is formed at the inclination end of the second guide 16i similarly to the first embodiment. In this needle unit, the projection 17a whose engagement has been released shifts from the state that it slides and contacts on a hole edge 16s on the projection movement terminal 16h side in the circumferential direction of the speed reducing portion 16r to a state that it slides and contacts on a hole edge 16t of the second guide 16i on the opposite side and reaches the projection movement terminal 16h, and due to this two-stage sliding resistance, the speed of the projection is reduced, whereby the impact when the projection 17a reaches the projection movement terminal 16h can be relaxed. In this needle unit, the section 16u near the engagement portion of the guide portion 16e is inclined, and this also causes sliding resistance and realizes impact relaxation.

In addition, in this needle unit, the speed reducing portion 16r is displaced to the circumferentially opposite side of the side where the projection movement terminal 16h is formed, and according to the displacement to the opposite side, the projection movement terminal 16h can be arranged collectively to the central side, and this makes die forming easier.

It is a matter of course that the speed reducing portion 16r is not limited to have a fixed inclination, and it can be folded so as to face circumferentially one side and the other side.

In addition, the needle unit of this fourth embodiment includes the following two contrivances. As a first contrivance, the support member 15 to which the needle 2 is fitted and attached is assembled rotatably around the axis, and if the tube 5 attached to the support member 15 is twisted, the twisting is easily eliminated by rotating the support member 15 relatively to the holding member 16 and the needle unit becomes easy to use.

The structure of this rotating mechanism is as follows. First, engagement pieces 16z are projectingly provided at a predetermined angle circumferentially on the inner peripheral surface of the base end of the holding member 16, and each engagement piece 16z is formed into a tapered surface whose projecting amount increases toward the tip end side. On the other hand, at the tip end (the side to which the needle 2 sticks out) of the support member 15, a swell-out portion 15a whose diameter becomes smaller toward the tip end side is formed, and this swell-out portion 15a is forcibly fitted in the engagement piece 16z, whereby the support member 15 is fitted and attached rotatably around the axis while being prevented from coming off the holding member 16. Furthermore, a fit-in prohibiting piece 15b is projectingly formed on the outer peripheral surface of the support member 15 so as to prohibit fitting-in of the support member 15 more than necessary.

As a second contrivance, incorporation of the covering member 17 from the tip end side of the holding member 16 is made easier. Namely, in the covering member 17, a slit 17b is formed toward the tip end side while including the projection 17a except for the base end side, and thereby, the projection 17a can be pushed-in and deformed in an elastically restorable manner. The covering member 17 can be easily incorporated in the holding member 16 by inserting the projection 17a from the tip end side of the holding member 16 while pushing-in and deforming the projection.

Furthermore, in this invention, the shape of the second guide 16c that leads the projection 17a circumferentially is not limited to the shape formed by folding straight the guide 16e, and it can also be formed into an arced shape as shown in, for example, FIG. 28, or can be formed by combining an arced portion and a straight portion.

In this fourth embodiment, a returning movement limiting portion 16m and a return preventive guide 16j corresponding to the returning movement limiting portion 4m and the return preventive guide 4j of the first embodiment, respectively, are formed. The returning movement limiting portion 16m is spaced from the returning movement terminal 16w (greatly displaced upward of FIG. 29 (toward the continuing section 16p side)). Namely, the returning movement limiting portion 16m is formed at the tip end of the first guide 16l while leaving a space T circumferentially and in the front and rear directions from the projection 17a positioned at the projection movement terminal 16h, and thereby, the range limiting the returning movement including the circumferential direction of the projection 17a can be formed as a space T having a width circumferentially wider than in the case like the first embodiment where the range is formed immediately adjacent to the returning movement terminal 16w of the return preventive guide 16j, whereby the returning movement of the projection 17a can be widely limited.

In this needle unit, on the returning movement limiting portion 16m, a movement urging portion 16x that is more inclined toward the returning movement terminal 16w with respect to the base end side and urges the projection 17a to move to the returning movement terminal 16w side is formed.

Furthermore, the invention can be carried out by fifth and sixth embodiments shown in FIG. 30 (A) and FIG. 30(B). In these needle units, a return restricting portion 16y is formed on the base end portion of the second guide 16i formed so as to incline straight or in an arc shape, and is provided on the side circumferentially opposite to the circumferential direction in which the second guide 16i guides the projection to the projection movement terminal 16h, and engages with the projection 17a to restrict it from returning to the first guide 16l side when the projection 17a is guided by (slidingly contacts) the second guide 16i or in a state close to this, whereby the returning movement of the projection 17a to the first guide 16l side can be reduced further.

BRIEF DESCRIPTION OF THE DRAWINGS

FIG. 2 (A) and (B) are a plan view and a front view, respectively, of the medical needle unit whose covering member is in a covering posture;

FIGS. 5 (A) and (B) are a plan view and a front cross-sectional view, respectively, of a needle;

FIGS. 7 (A), (B) and (C) are a plan view, a front cross-sectional view and a side view, respectively, of the covering member;

FIGS. 16 (A) and (B) are partial enlarged views of side cross sectional view and a front cross sectional view of the holding member provided with a thick portion;

FIGS. 20 (A) and (B) are front views showing a housed posture and a covering posture of the fourth embodiment, respectively;

FIG. 21 is an exploded view of the medical needle unit of the fourth embodiment;

FIGS. 22 (A), (B), and (C) are plan view, a side view, and a front view of the holding member of the fourth embodiment, respectively;

FIGS. 23 (A), (B), and (C) are a plan view, a front view, and a side view of the covering member of the fourth embodiment, respectively;

FIGS. 26 (A) and (B) are a partial front view of the covering member, and a partial front view showing a state that the covering member is incorporated in the holding member of the fourth embodiment;

EXPLANATION OF SYMBOLS

Figure 1:
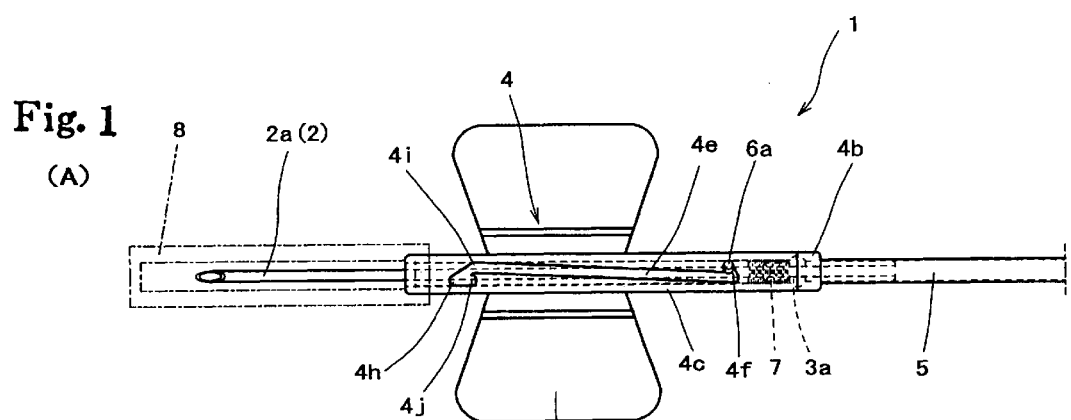
FIG. 1 (A) and (B) are a plan view and a front view, respectively, of a medical needle unit whose covering member is in a housed posture.
Figure 1:
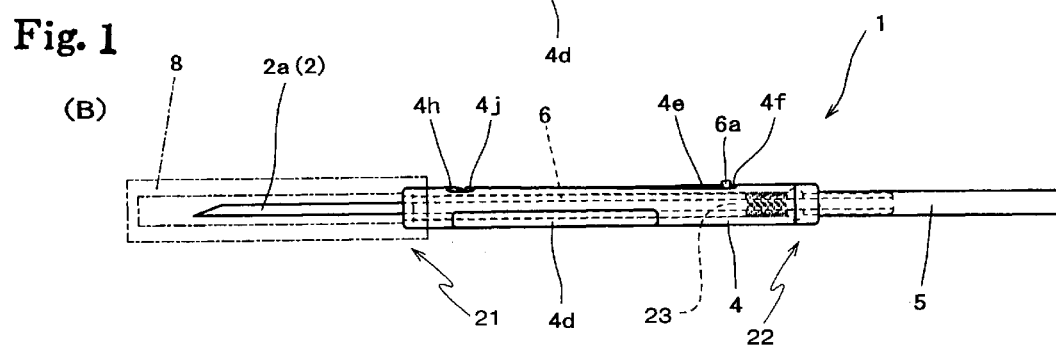
Figure 3:
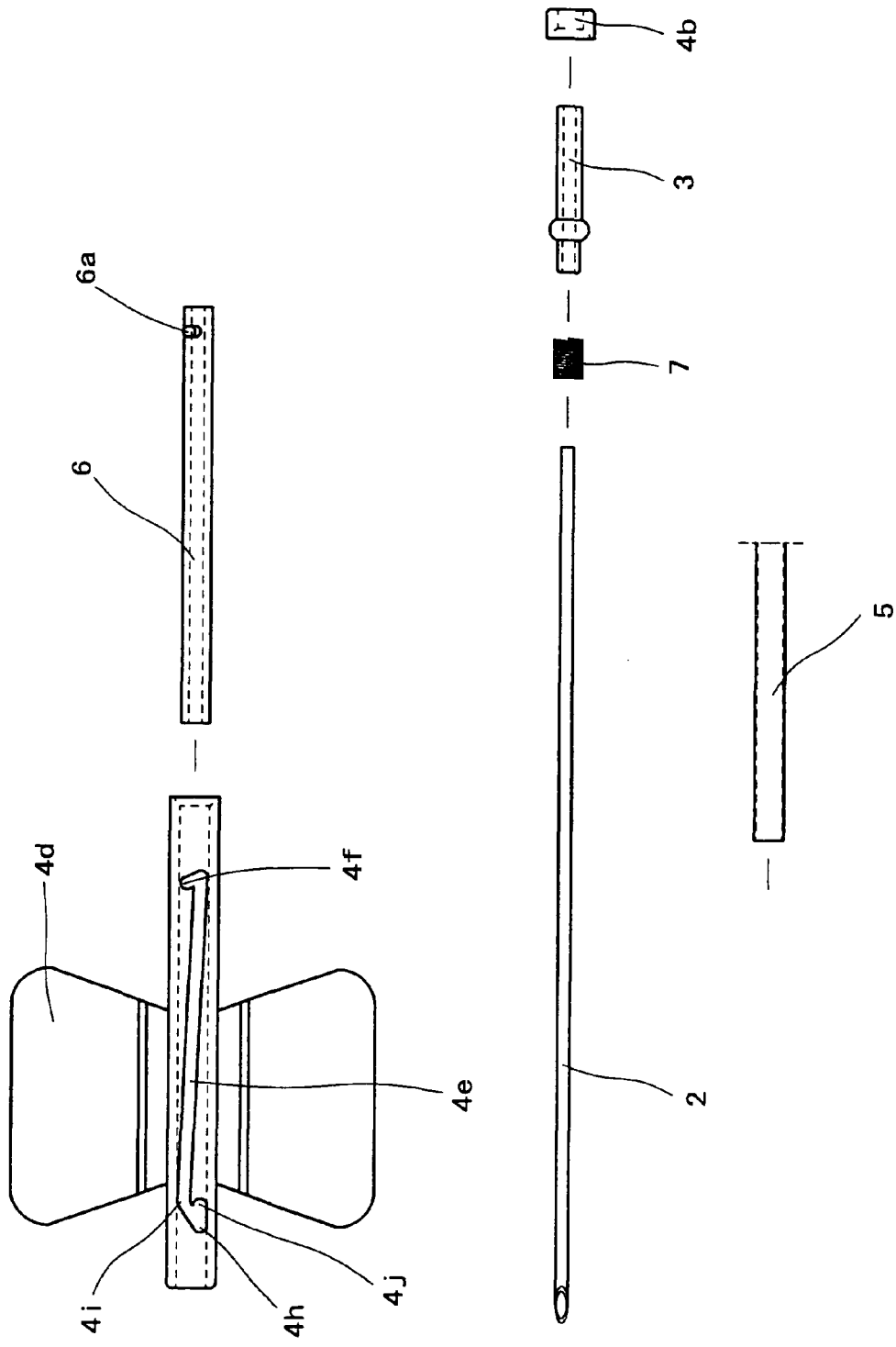
FIG. 3 is an exploded view of the medical needle unit.
Figure 4:
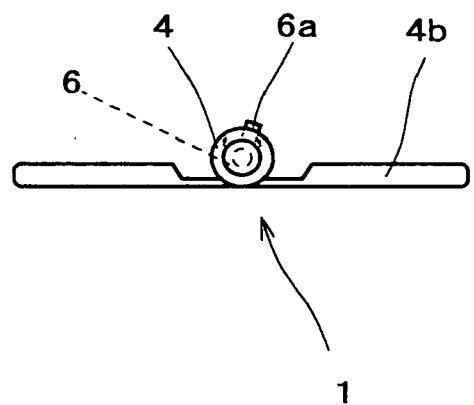
FIGS. 4 (A) and (B) are side views of the medical needle unit.
Figure 4:
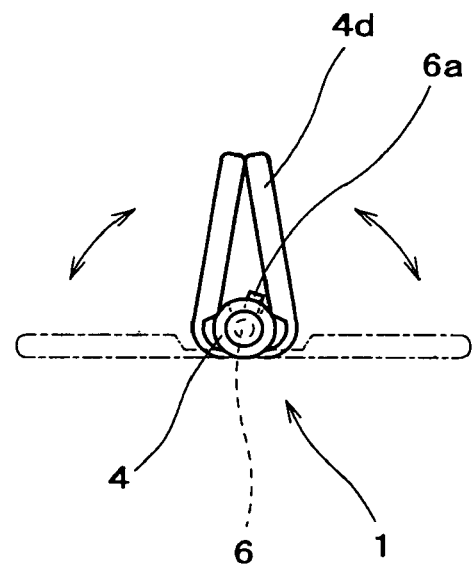
Figure 6:
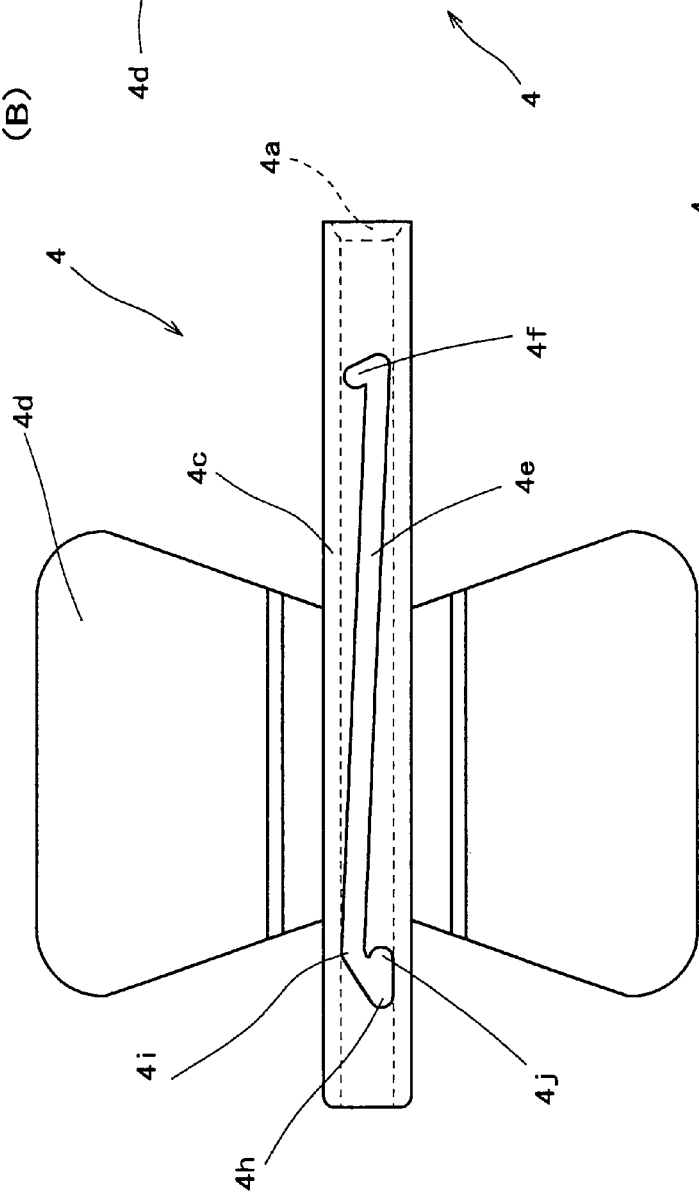
FIGS. 6 (A), (B), and (C) are a plan view, a side view, and a front view, respectively, of a holding member.
Figure 6:
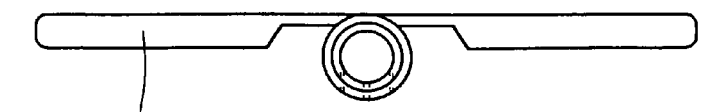
Figure 6:
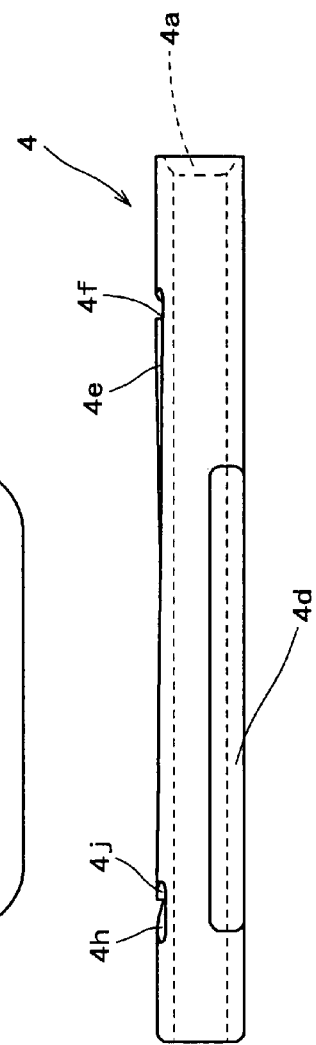
Figure 8:
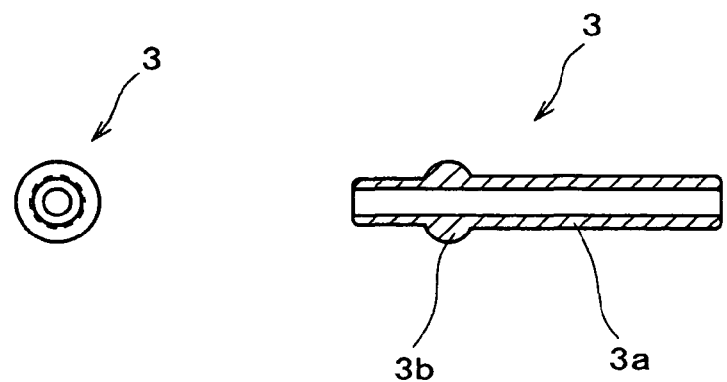
FIGS. 8 (A) and (B) a side view and a front cross-sectional view of a support member, and Figs. (C) and (D) are a side view and a front cross-sectional view of a lid, respectively.
Figure 8:
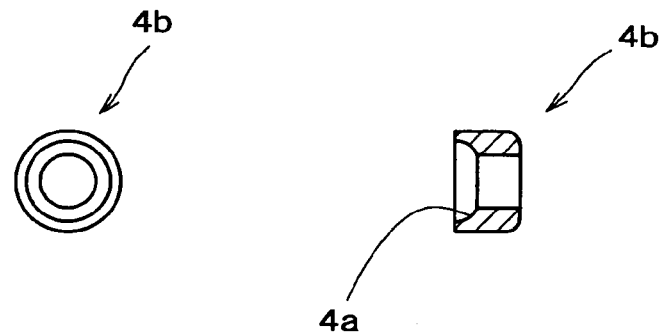
Figure 9:
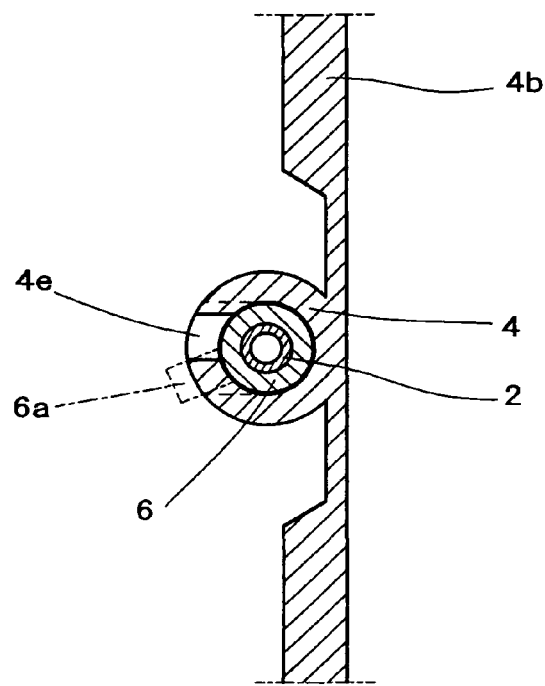
FIGS. 9 (A) and (B) are partial enlarged views of a side cross-sectional view and a front cross-sectional view, respectively, of the medical needle unit.
Figure 9:
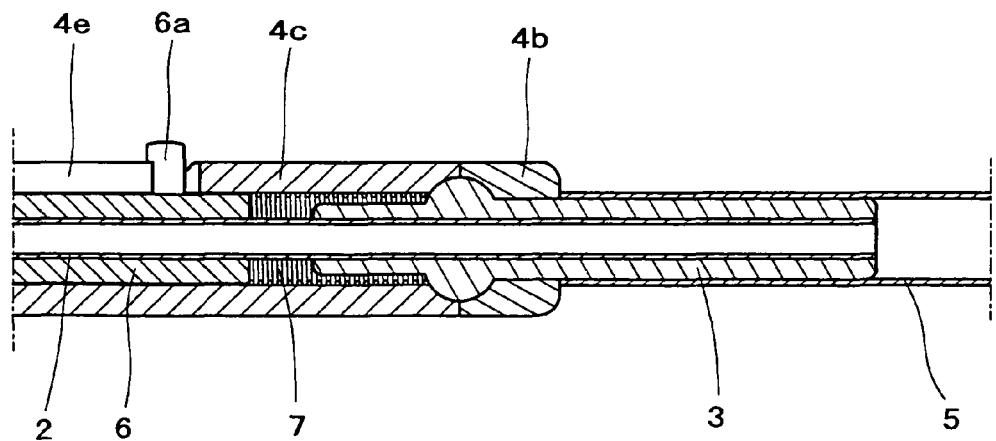
Figure 10:
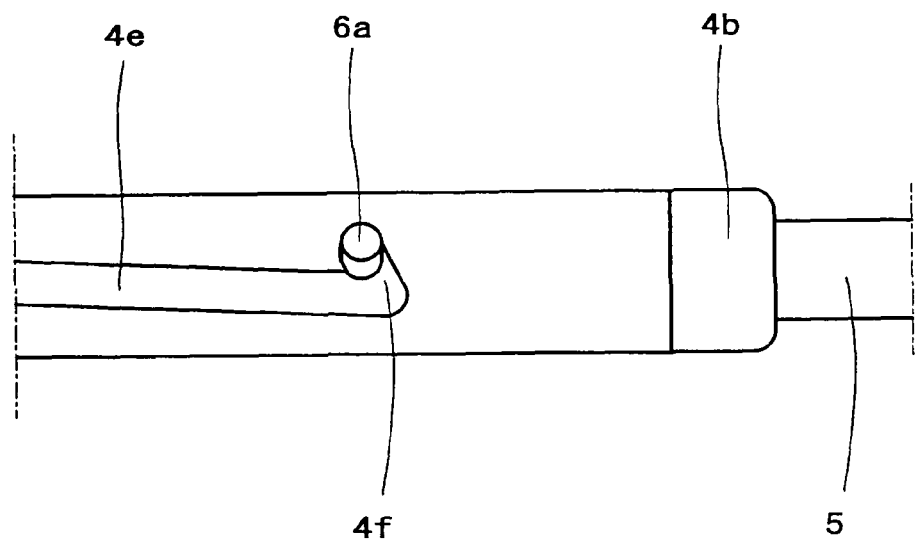
FIGS. 10 (A) and (B) are partial enlarged view of plan views of the medical needle unit, showing an engaging mechanism and a stopper mechanism of a first embodiment, respectively.
Figure 10:
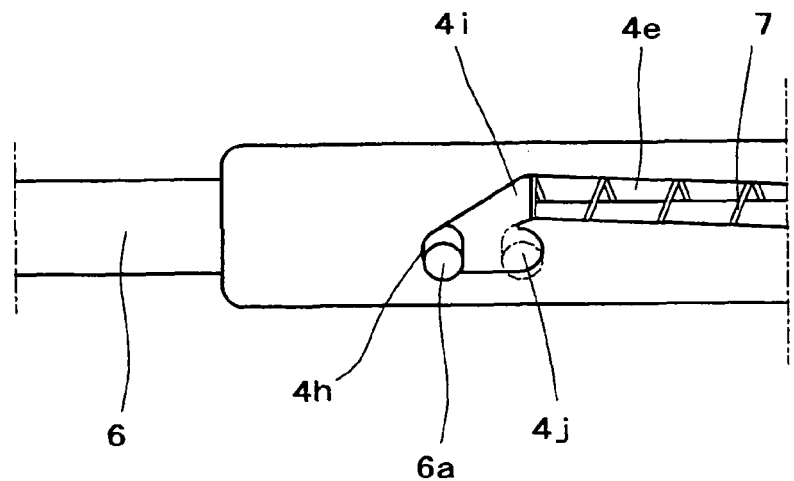
Figure 11:
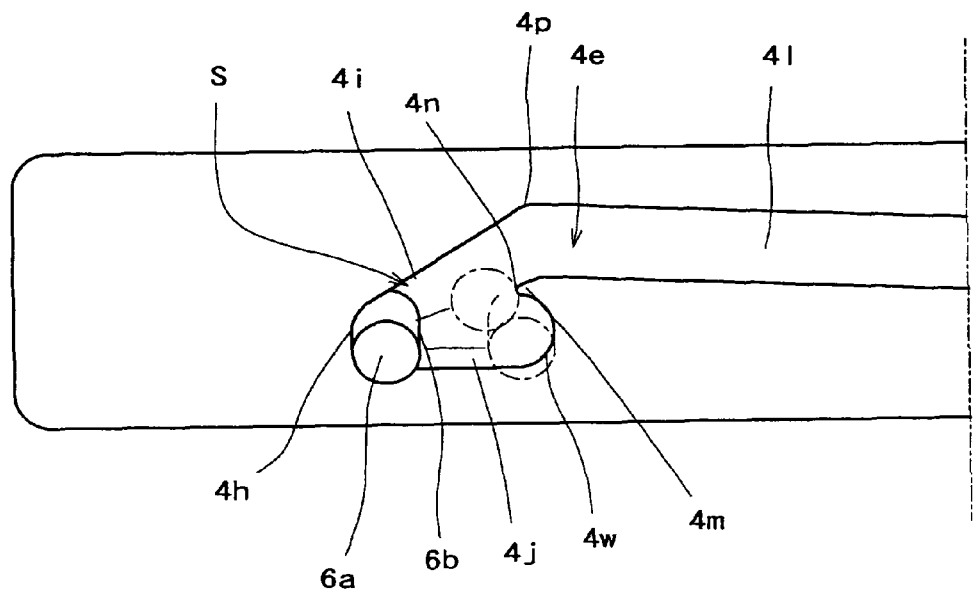
FIGS. 11 (A) and (B) are action explanatory views showing the relationship between the projection and the guide portion, showing the first embodiment and a modified embodiment thereof.
Figure 11:
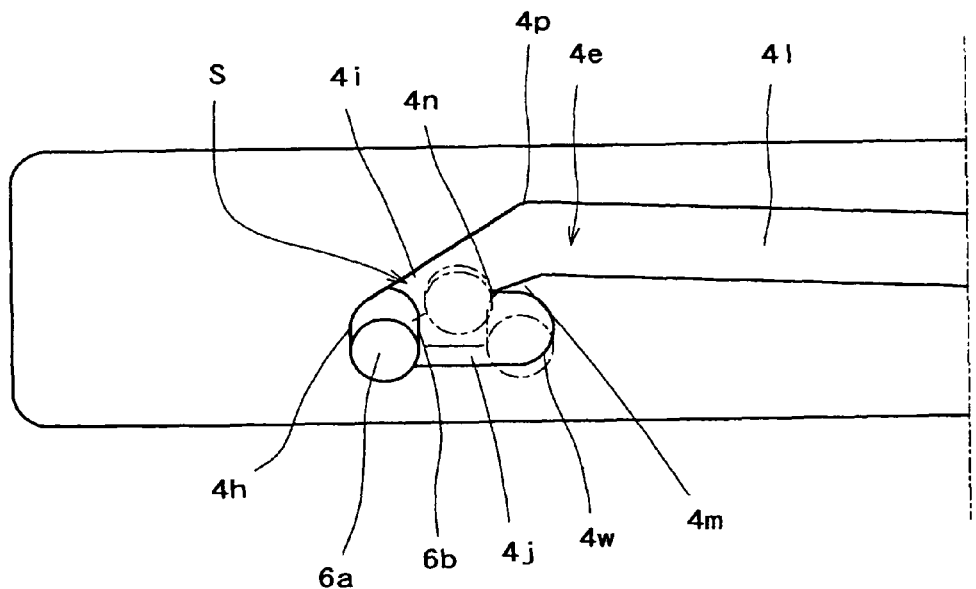
Figure 12:
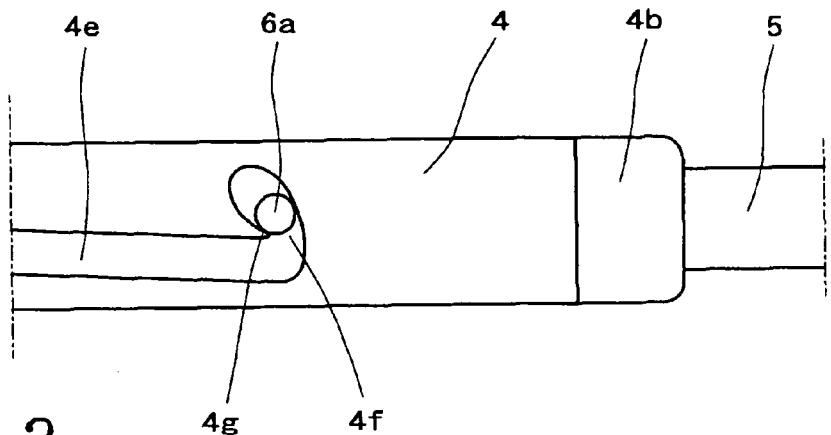
FIGS. 12 (A), (B), and (C) are partial enlarged view of plan views showing other examples of the engaging mechanism of the first embodiment, respectively.
Figure 12:
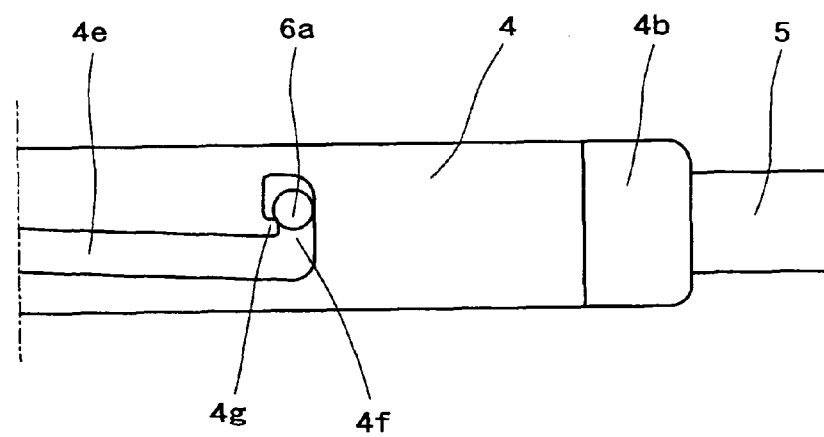
Figure 12:
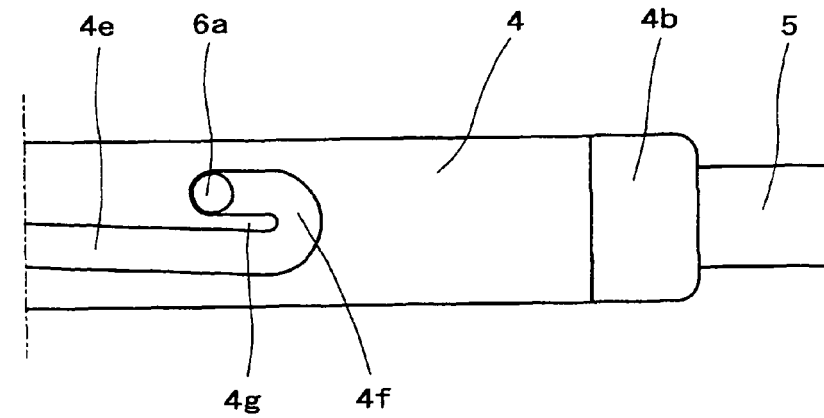
Figure 13:
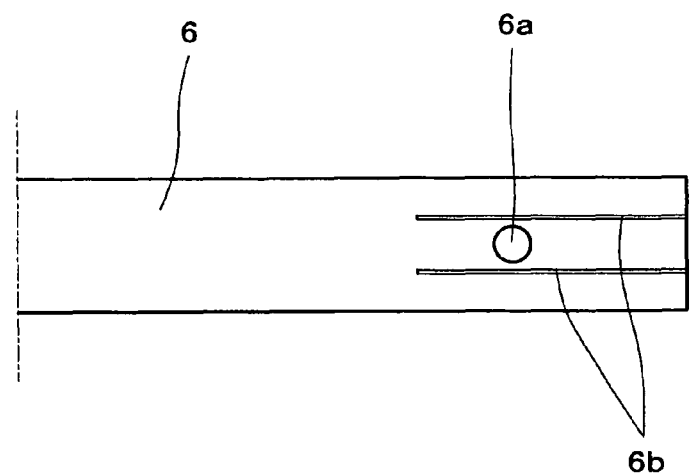
FIGS. 13 (A) and (B) area partial enlarged views of a plan view of the covering member and a front cross-sectional view of the covering member incorporated in the holding member, respectively.
Figure 13:
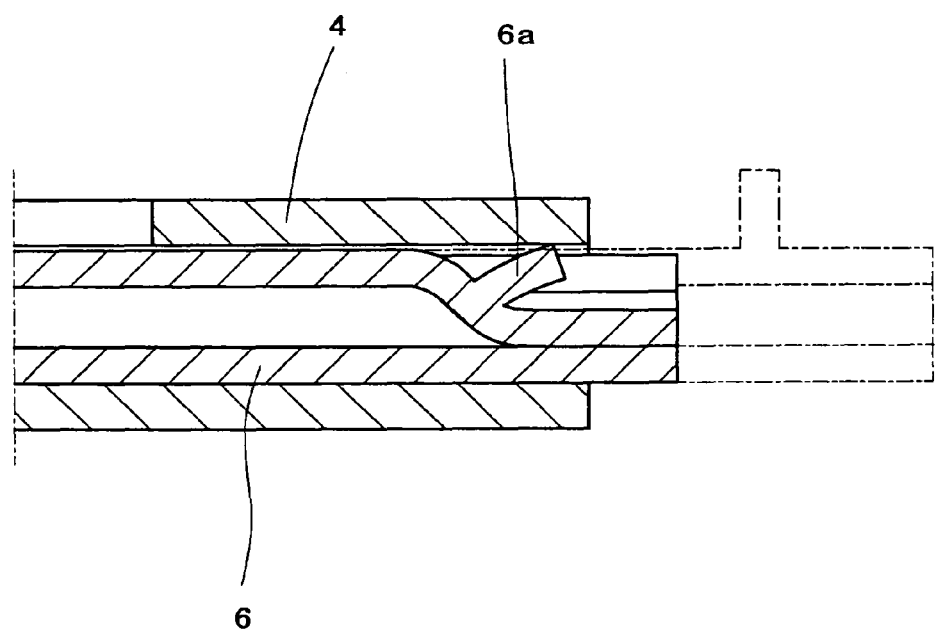
Figure 14:
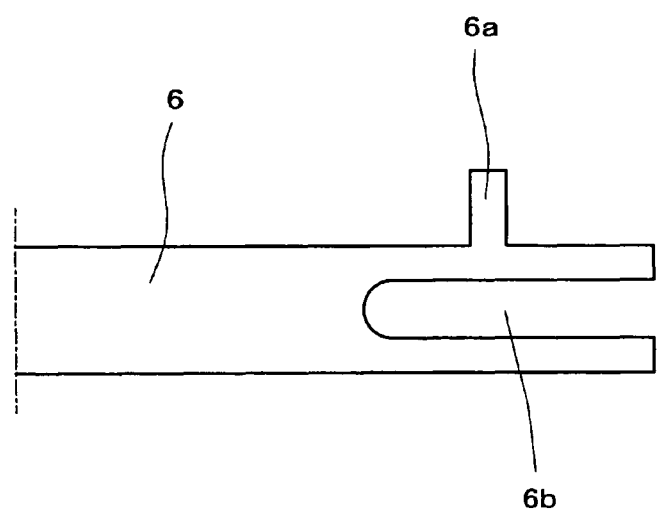
FIGS. 14 (A) and (B) are a partial plan view of the covering member and a partial longitudinal sectional view of the covering member incorporated in the holding member, respectively.
Figure 14:
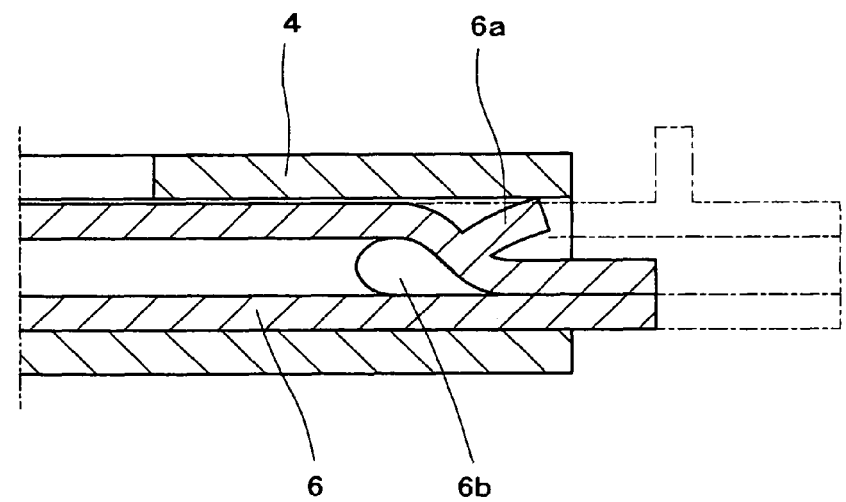
Figure 15:
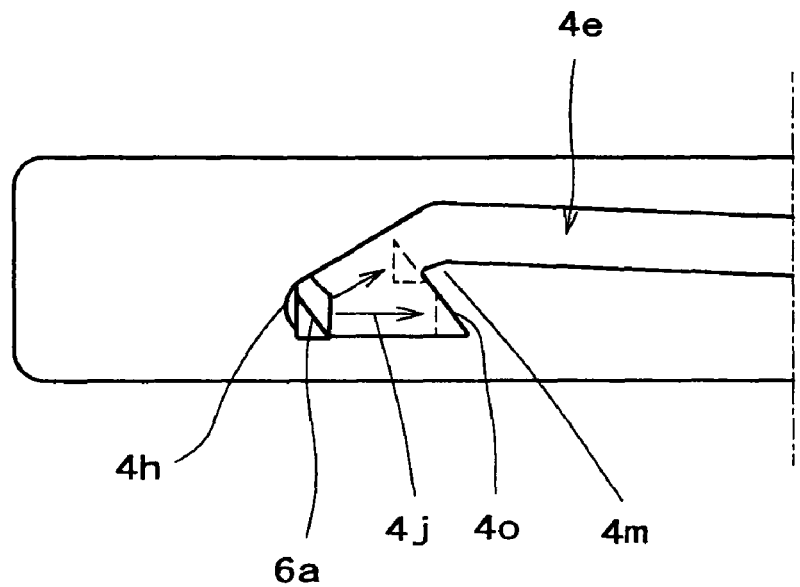
FIG. 15 (A) and (B) are partial enlarged views of a plan cross sectional views showing other examples of the projection.
Figure 15:
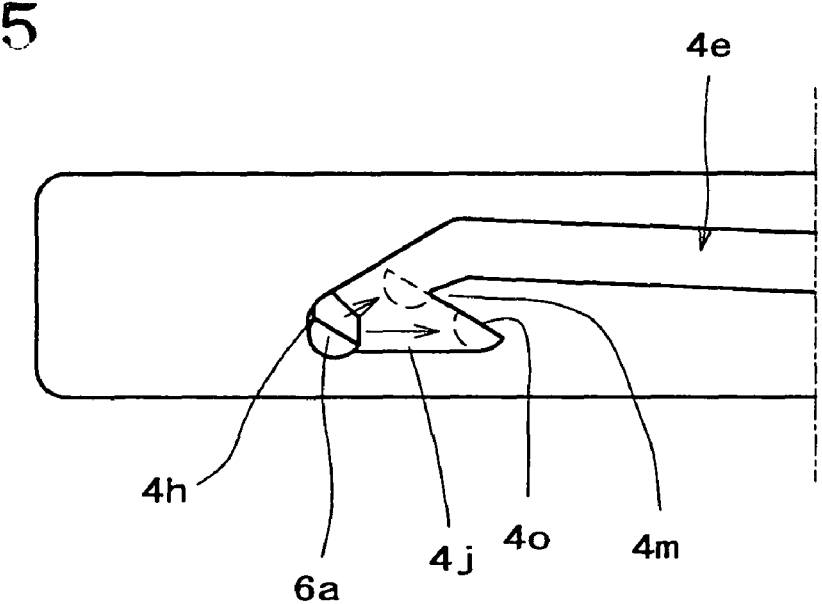
Figure 1:
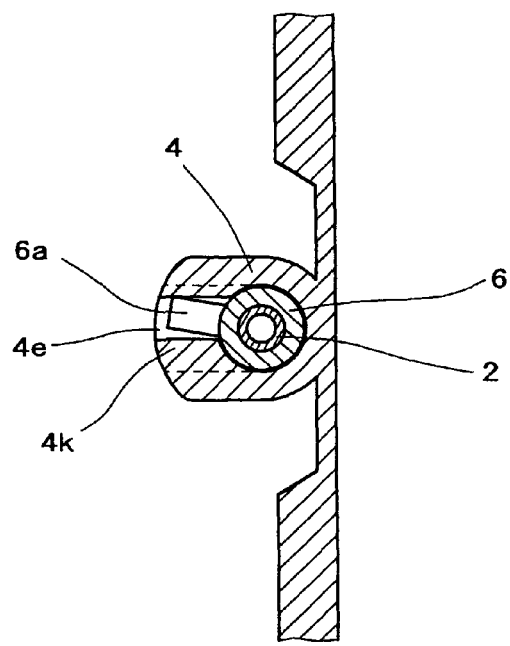
Figure 1:
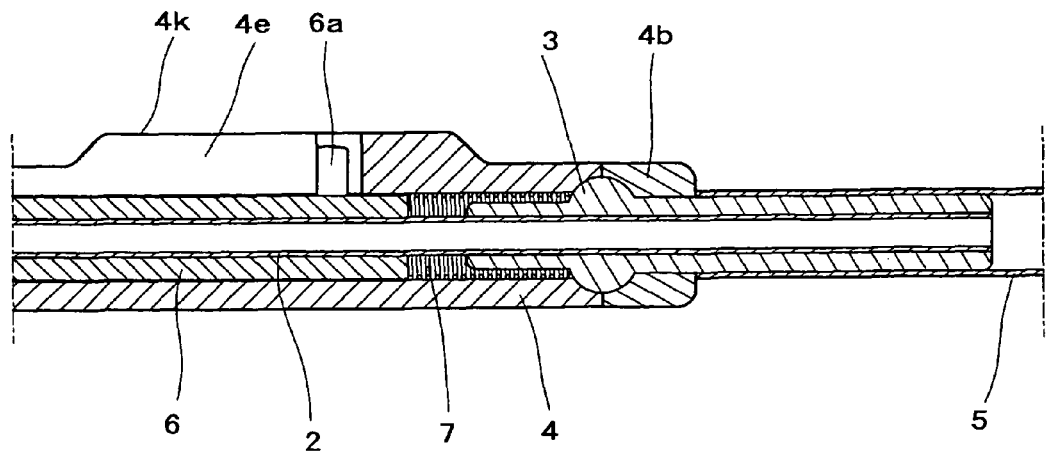
Figure 17:
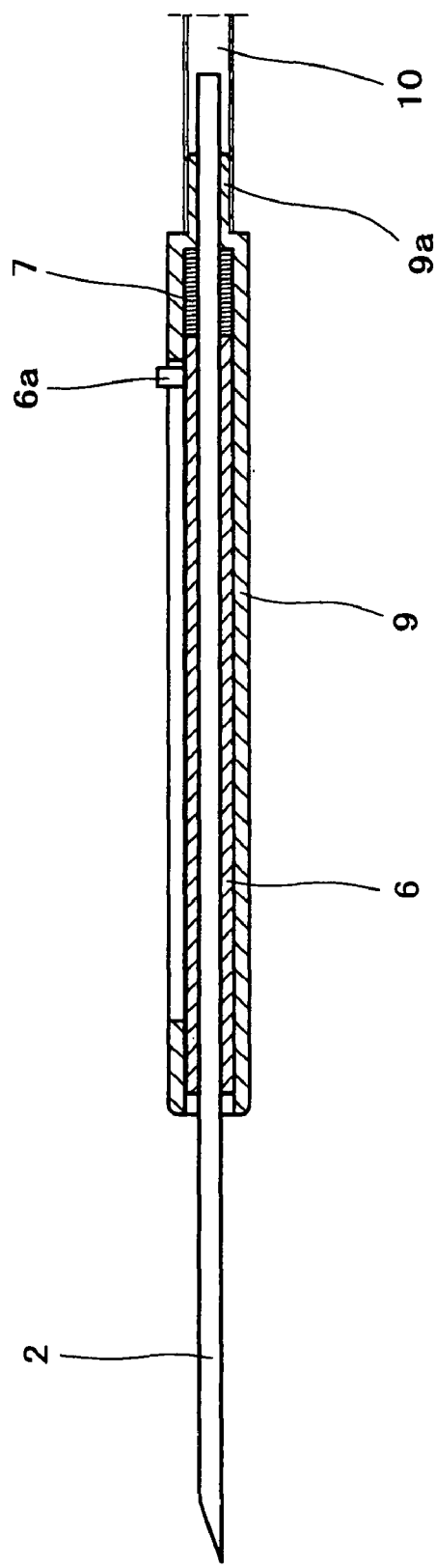
FIG. 17 is a a front cross sectional view showing the second embodiment.
Figure 18:
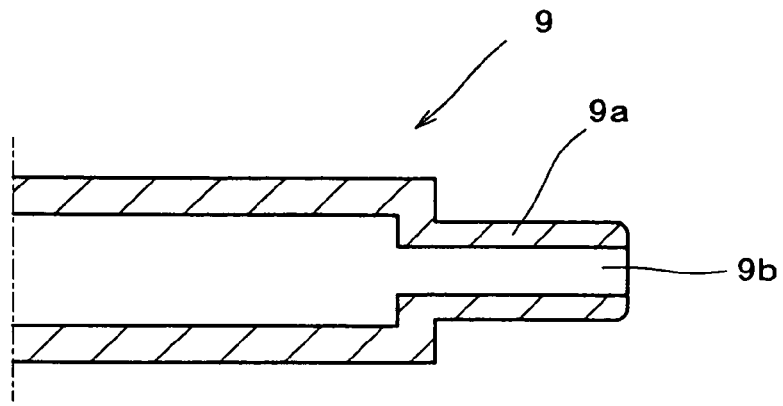
FIGS. 18 (A), (B), and (C) are partial enlarged views of front cross sectional views of holding members respectively.
Figure 18:
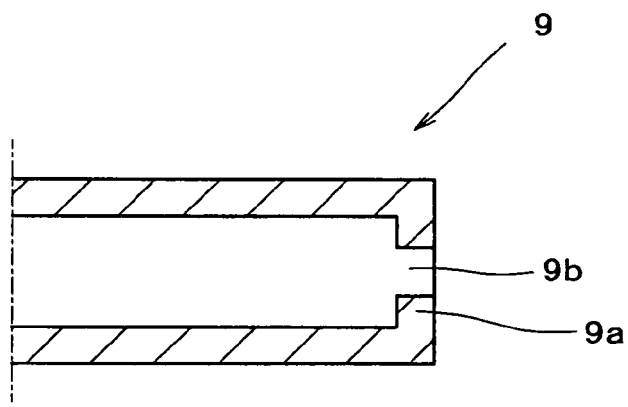
Figure 18:
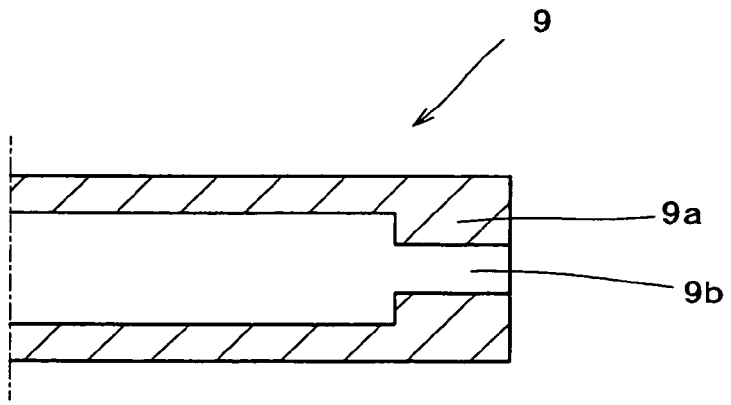
Figure 19:
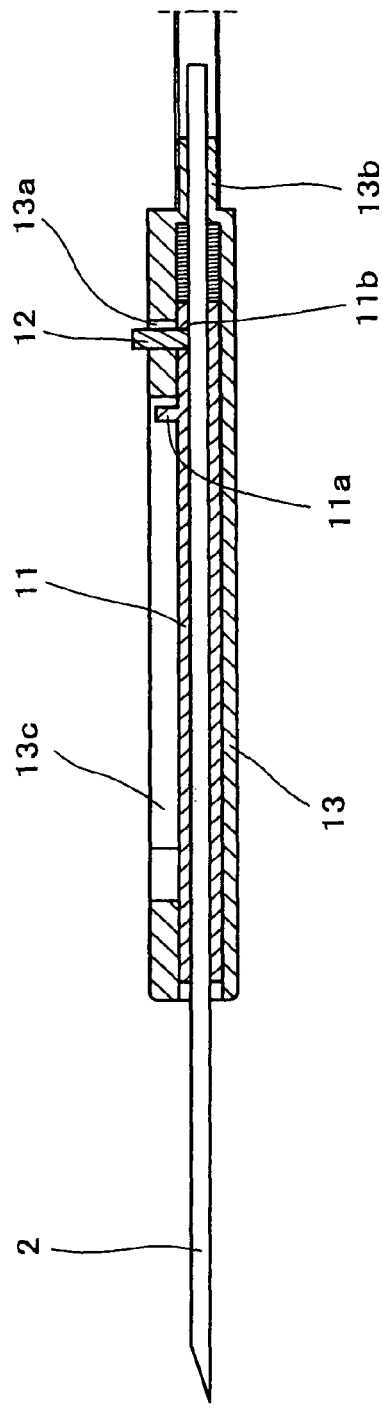
FIGS. 19 (A) and (B) are front cross sectional views showing a housed posture and a covering posture of the third embodiment, respectively.
Figure 19:
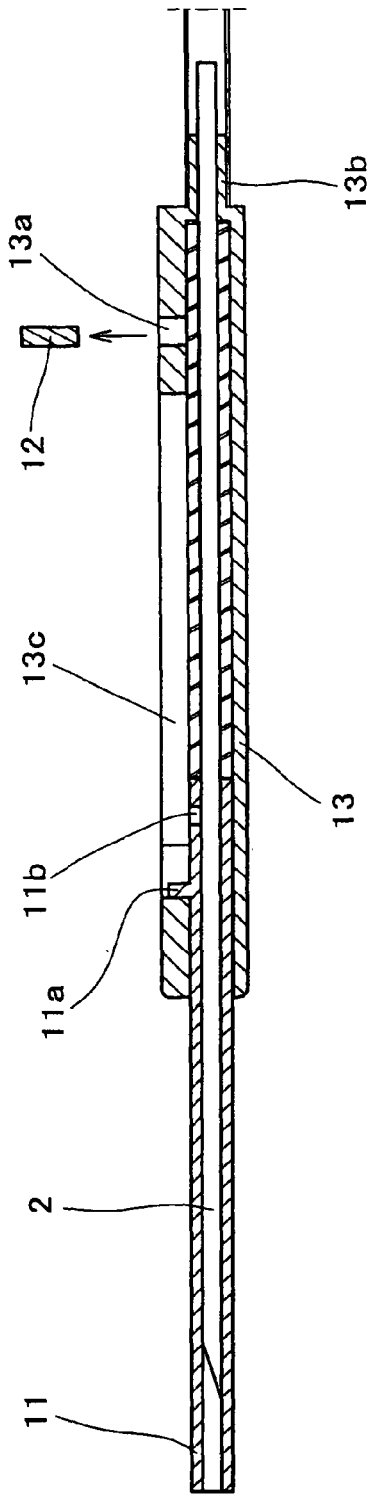
Figure 24:
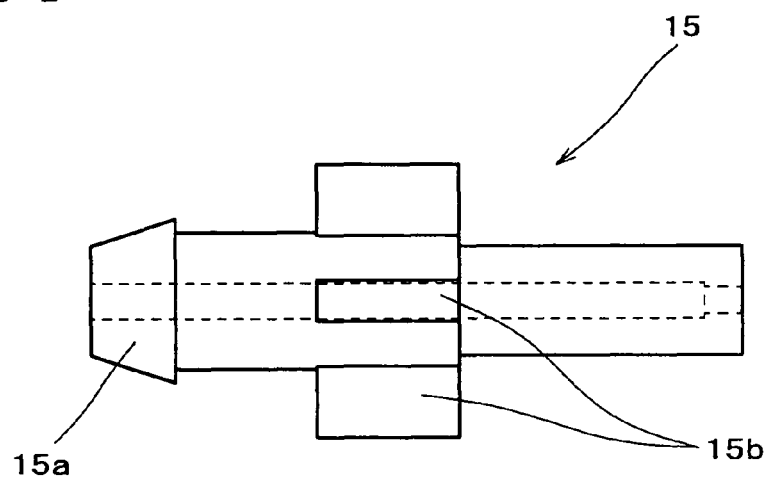
FIGS. 24 (A), (B), and (C) are a front view, a left side view and a right side view of the support member of the fourth embodiment, respectively.
Figure 24:
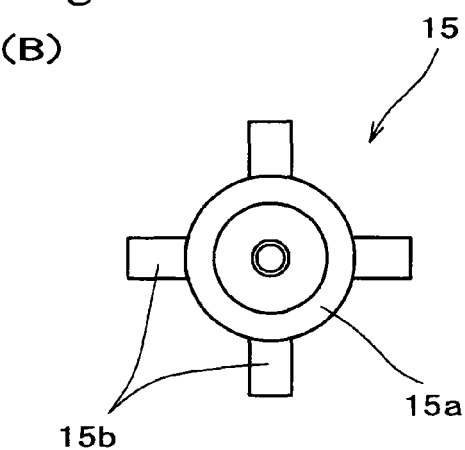
Figure 24:
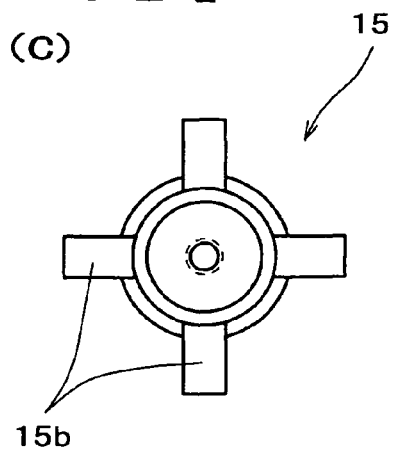
Figure 25:
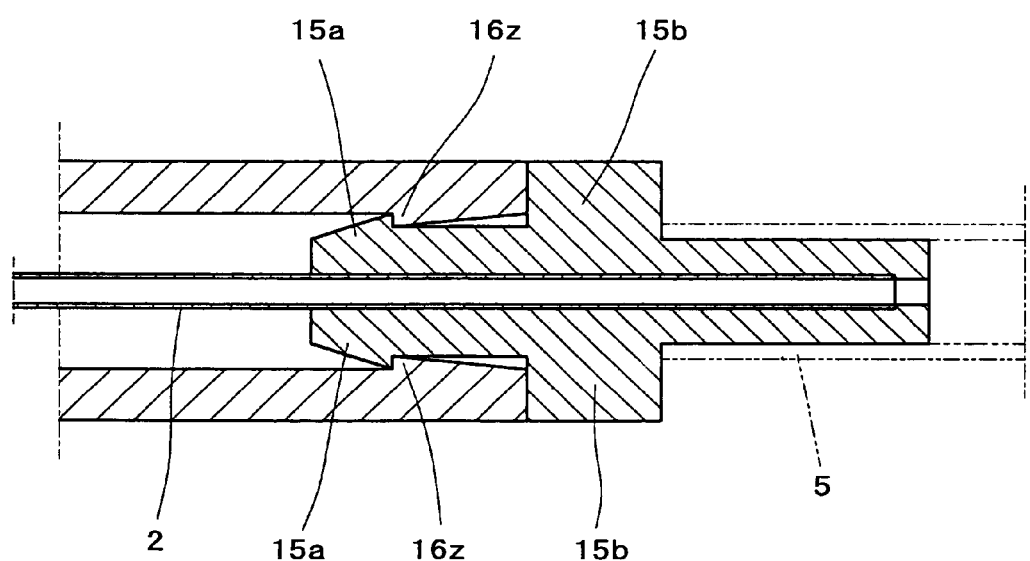
FIG. 25 is a partial enlarged view of a front cross sectional view of the medical needle unit showing the state that the support member fits in the holding member.
Figure 27:
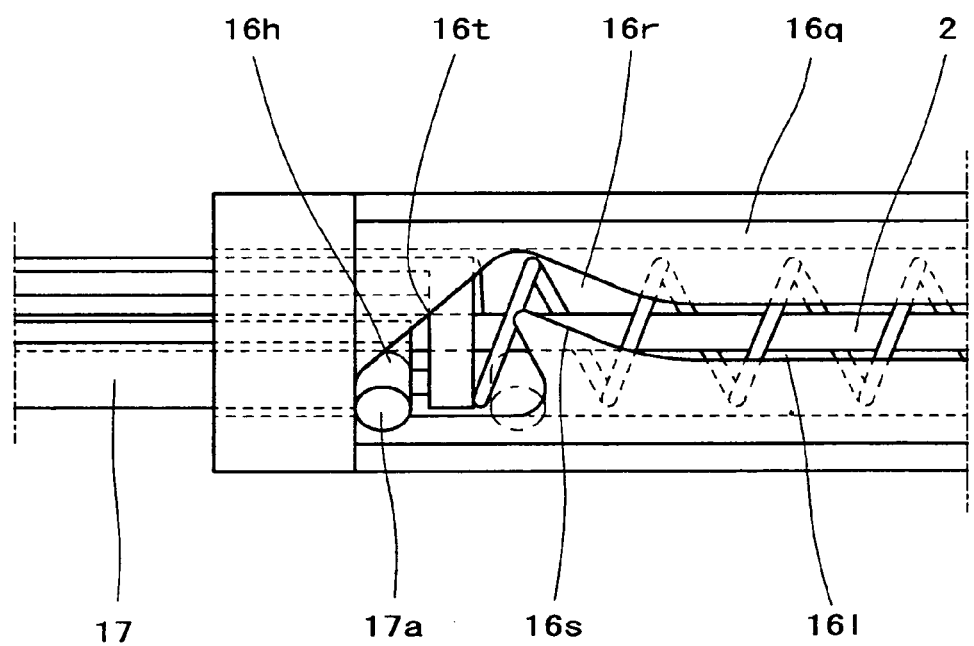
FIG. 27 is a partial enlarged view of a plan view of the medical needle unit of the fourth embodiment, showing a state that the covering member is positioned in the covering posture.
Figure 28:
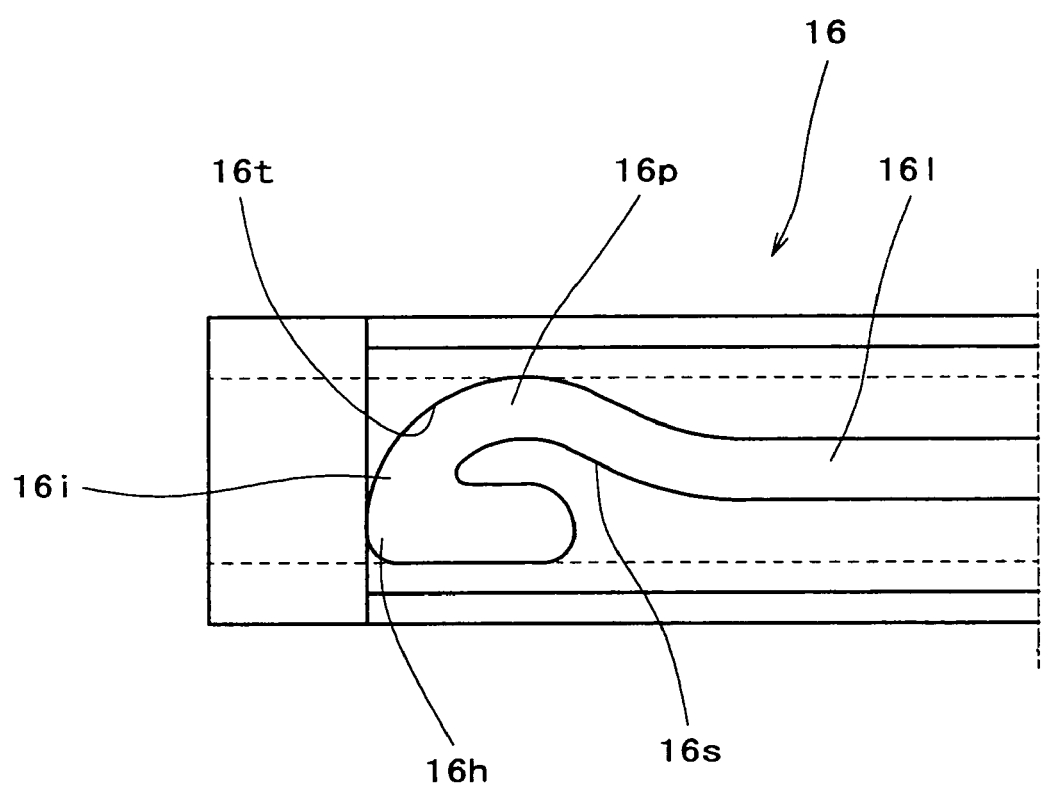
FIG. 28 is a partial enlarged view of a plan view showing another example of the engagement portion.
Figure 29:
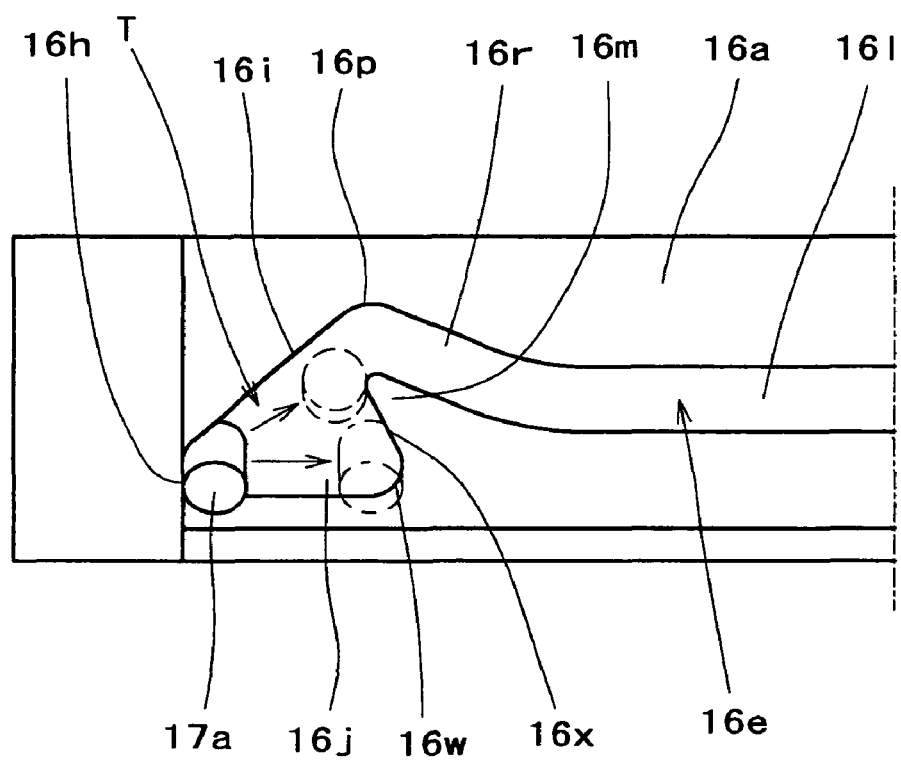
FIG. 29 is an action explanatory view showing the relationship between the projection and the guide portion of the fourth embodiment.
Figure 30:
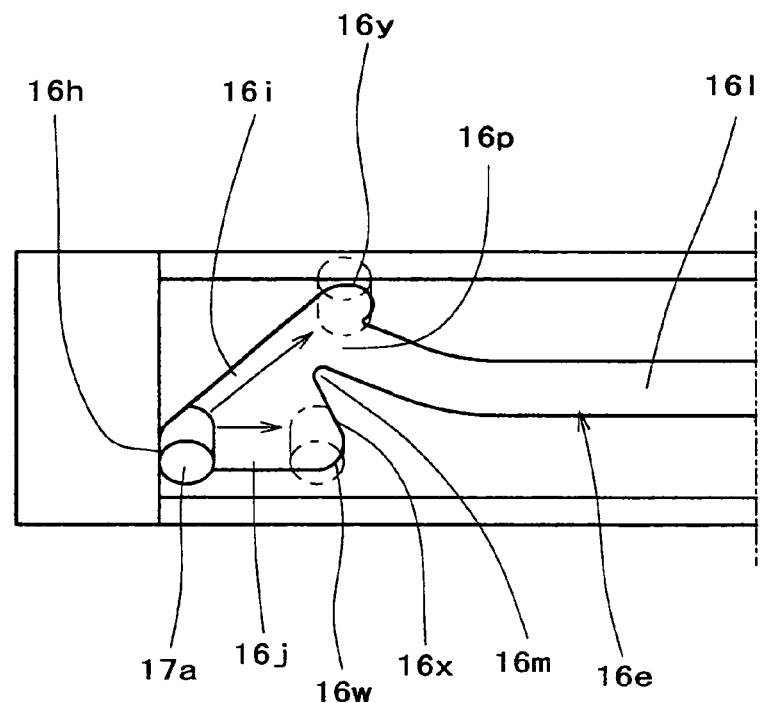
FIGS. 30 (A) and (B) are action explanatory views showing the relationship between the projection and the guide portion of the fifth and sixth embodiments.
Figure 30:
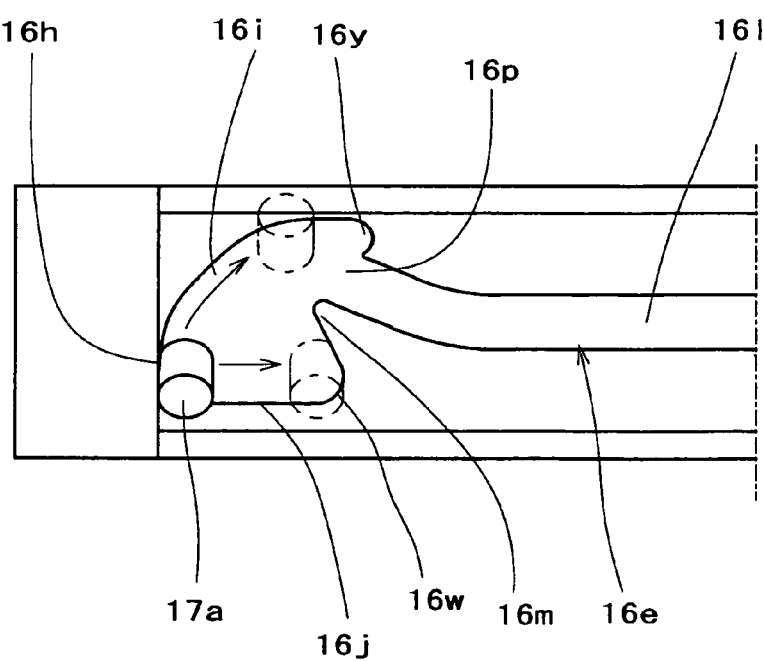

1: medical needle unit
2: needle
2a: exposed portion
4, 16: holding member
4a: holding portion
4c: holding portion main body
4e, 16e: guide portion
4h, 16h: projection movement terminal
4i, 16i: second guide
4j, 16j: return preventive guide
4l, 16l: first guide
4m, 16m: returning movement limiting portion
4n: movement limiting portion tip end
4p, 16p: continuing section
4w, 16w: returning movement terminal
6, 17: covering member
6a, 17a: projection
7: spring 16s: speed reducing portion
16x: movement urging portion
16y: return restricting portion

What is claimed is:

1. A medical needle unit comprising:
a hollow needle;
a holding member formed so that its base end holds the needle base end and its main body covers the needle while having a space between the holding member and the needle, and a needle tip end sticks out from a main body tip end;
a covering member that is provided in the space between the holding member main body and the needle, and is movable with respect to the holding member between a housed posture and a covering posture, the housed posture being on the base end side in which the covering member is housed within the holding member main body while the needle tip end sticks out from the holding member main body, and the covering posture being on a tip end side in which the covering member sticks out from the holding member main body and covers the needle tip end;
a guide portion that is formed on the holding member main body so as to guide a projection formed on an outer peripheral surface of the covering member and enable the covering member to move between the housed posture and the covering posture;
an engaging mechanism that disengageably engages with the projection and holds the covering member in the housed posture, and allows the movement from the housed posture to the covering posture of the covering member according to disengagement of the projection; and
an urging member that forcibly moves the covering member to the covering posture, the projection of the covering member being disengaged from the engagement mechanism until the projection reaches the projection movement terminal of the guide portion, wherein
when a force is applied to push-back the covering member against forcible movement by the urging member to the base end side with the projection being positioned at the projection movement terminal,
the projection is configured to prevent the covering member from moving to the base end side and prevent the needle tip from being exposed from the covering member,
the guide portion comprises a first guide joined to the engaging mechanism at the base end and formed to be a slot-shaped and long in the lengthwise direction of the needle inclined circumferentially to one direction and a second guide joined from a tip end of the first guide inclined or curved circumferentially to the other direction and guides the projection through the first guide which is inclined circumferentially to one direction to the projection movement terminal while leading this projection along the inclined shape or curved shape circumferentially to the other direction with respect to the holding member, and
the holding member main body is provided with a return preventive guide that faces the projection movement terminal while being positioned in the second guide side rather than the tip end of the first guide, and allows the projection to return to the base end side within a range that the needle tip does not stick out from the covering member when a force is applied to push-back the covering member whose projection is positioned at the projection movement terminal to the base end side, and a returning movement limiting portion that is positioned closer to the base end side than the projection movement terminal is to the base end side, the projection movement terminal is closer to the tip end side than the returning movement terminal of the return preventive guide is to the tip end side, and the returning movement limiting portion is positioned at the tip end side of the first guide while being spaced toward the base end side from the projection positioned at the projection movement terminal, and restricts the returning movement of the projection toward the first guide side,
the returning movement limiting portion restricting the returning movement of the projection toward the first guide side by contacting with the projection when a force to push-back the covering member toward the base end side is applied and thereby restricting movement of the projection positioned at the projection movement terminal moves toward the tip end of the first guide.

2. The medical needle unit according to claim 1, wherein a movement urging portion that urges the projection to move to the returning movement terminal is provided between the returning movement limiting portion and a returning movement terminal of the return preventive guide.

3. The medical needle unit according to claim 1, wherein the returning movement limiting portion is a tip end portion of the first guide.

4. The medical needle unit according to claim 1, wherein the second guide is provided with a return restricting portion on the opposite side to the leading side to the second guide in the circumferential direction with respect to the first guide, said return restricting portion restricting the projection from moving to the opposite side of the circumferential direction over the first guide tip end position and returning to the first guide when the projection is doing returning-back movement while sliding and contacting on the second guide.

5. The medical needle unit according to claim 2, wherein the returning movement limiting portion is a tip end portion of the first guide.

6. The medical needle unit according to claim 2, wherein the second guide is provided with a return restricting portion on the opposite side to the leading side to the second guide in the circumferential direction with respect to the first guide, said return restricting portion restricting the projection from moving to the opposite side of the circumferential direction over the first guide tip end position and returning to the first guide when the projection is doing returning-back movement while sliding and contacting on the second guide.

7. The medical needle unit according to claim 3, wherein the second guide is provided with a return restricting portion on the opposite side to the leading side to the second guide in the circumferential direction with respect to the first guide, said return restricting portion restricting the projection from moving to the opposite side of the circumferential direction over the first guide tip end position and returning to the first guide when the projection is doing returning-back movement while sliding and contacting on the second guide.

8. The medical needle unit according to claim 5, wherein the second guide is provided with a return restricting portion on the opposite side to the leading side to the second guide in the circumferential direction with respect to the first guide, said return restricting portion restricting the projection from moving to the opposite side of the circumferential direction over the first guide tip end position and returning to the first guide when the projection is doing returning-back movement while sliding and contacting on the second guide.

* * * * *